United States Patent
Albahar et al.

(10) Patent No.: US 11,866,397 B1
(45) Date of Patent: Jan. 9, 2024

(54) PROCESS CONFIGURATIONS FOR ENHANCING LIGHT OLEFIN SELECTIVITY BY STEAM CATALYTIC CRACKING OF HEAVY FEEDSTOCK

(71) Applicant: Saudi Arabian Oil Company, Dhahran (SA)

(72) Inventors: Mohammed Z. Albahar, Dhahran (SA); Emad N. Al-Shafei, Dhahran (SA); Mohammed F. Aljishi, Dhahran (SA); Ali N. Aljishi, Dhahran (SA); Ali S. Alnasir, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 18/183,498

(22) Filed: Mar. 14, 2023

(51) Int. Cl.
*C07C 4/06* (2006.01)
*B01J 38/36* (2006.01)

(52) U.S. Cl.
CPC ............... *C07C 4/06* (2013.01); *B01J 38/36* (2013.01); *C07C 2529/40* (2013.01)

(58) Field of Classification Search
CPC ......... C07C 4/06; C07C 2529/40; B01J 38/36
See application file for complete search history.

(56) References Cited

U.S. PATENT DOCUMENTS

| | | | |
|---|---|---|---|
| 3,725,495 A | 4/1973 | Wrisberg et al. | |
| 3,839,485 A | 10/1974 | Wrisberg et al. | |
| 4,172,816 A * | 10/1979 | Pop | B01J 29/20 585/653 |
| 6,166,279 A * | 12/2000 | Schwab | C07C 11/06 585/312 |
| 6,340,429 B1 * | 1/2002 | Minkkinen | C10G 70/00 585/650 |
| 6,743,961 B2 | 6/2004 | Powers | |
| 7,578,929 B2 | 8/2009 | Stell et al. | |
| 9,284,497 B2 | 3/2016 | Bourane et al. | |
| 9,284,502 B2 | 3/2016 | Bourane et al. | |
| 9,382,486 B2 | 7/2016 | Bourane et al. | |
| 9,670,418 B2 * | 6/2017 | Schmidt | C10G 9/36 |

(Continued)

FOREIGN PATENT DOCUMENTS

| | | |
|---|---|---|
| CA | 2877163 A1 | 2/2014 |
| DE | 112020000884 B4 | 6/2022 |

(Continued)

*Primary Examiner* — Ali Z Fadhel
(74) *Attorney, Agent, or Firm* — DINSMORE & SHOHL LLP

(57) ABSTRACT

A process for upgrading a hydrocarbon feed to produce light olefins, includes contacting the hydrocarbon feed with steam in the presence of a cracking catalyst in a steam catalytic cracking reactor at reaction conditions sufficient to cause at least a portion of the hydrocarbons in the hydrocarbon feed to undergo one or more cracking reactions to produce a steam catalytic cracking effluent comprising ethylene, propylene, or both, wherein the process is capable of being transitioned between an ethylene-selective mode and a propylene-selective mode; determining whether to produce ethylene or propylene; when producing ethylene, then operating the process in ethylene-selective mode comprises producing more ethylene than propylene; or when producing propylene, then operating the process in propylene-selective mode comprises producing more propylene than ethylene.

20 Claims, 4 Drawing Sheets

(56) References Cited

U.S. PATENT DOCUMENTS

| | | | |
|---|---|---|---|
| 11,066,605 B2 * | 7/2021 | Al-Shafei | B01J 29/90 |
| 11,066,606 B2 * | 7/2021 | Al-Shafei | B01J 8/02 |
| 11,090,643 B2 | 8/2021 | Al-Shafei et al. | |
| 11,370,731 B1 | 6/2022 | Al-Shafei et al. | |
| 2004/0004022 A1 * | 1/2004 | Stell | C10G 9/36 |
| | | | 208/132 |
| 2005/0148806 A1 * | 7/2005 | Cruijsberg | C10G 9/36 |
| | | | 585/652 |
| 2021/0301212 A1 * | 9/2021 | Al-Shafei | B01J 29/40 |
| 2021/0363438 A1 | 11/2021 | Al-Shafei et al. | |
| 2022/0017829 A1 * | 1/2022 | Al-Shafei | C10G 7/06 |

FOREIGN PATENT DOCUMENTS

| | | | |
|---|---|---|---|
| WO | 0132806 | A1 | 5/2001 |
| WO | 2013142609 | A1 | 9/2013 |

* cited by examiner

PROCESS CONFIGURATIONS FOR ENHANCING LIGHT OLEFIN SELECTIVITY BY STEAM CATALYTIC CRACKING OF HEAVY FEEDSTOCK

BACKGROUND

Field

The present disclosure relates to systems and processes for upgrading heavy hydrocarbon feeds, in particular, systems and processes for converting heavy hydrocarbon feeds through steam catalytic cracking to produce light olefins.

Technical Background

The worldwide increasing demand for light olefins remains a major challenge for many integrated refineries. In particular, the production of some valuable light olefins such as ethylene, propene, and butenes has attracted increased attention as purified olefin streams are considered the building blocks for polymer synthesis. The production of light olefins depends on several process variables, such as the feed type, operating conditions, and the type of catalyst. Despite the options available for producing a greater yield of propene and light olefins, intense research activity in this field is still being conducted.

Petrochemical feeds, such as crude oils, can be converted to petrochemicals, such as fuel blending components and chemical products and intermediates such as light olefins and light aromatic compounds, which are basic intermediates for a large portion of the petrochemical industry. Crude oil is conventionally processed by distillation followed by various reforming, solvent treatments, and hydroconversion processes to produce a desired slate of fuels, lubricating oil products, chemicals, chemical feedstocks and the like. An example of a conventional refinery process includes distillation of crude oil by atmospheric distillation to recover gas oil, naphtha, gaseous products, and an atmospheric residue. Streams recovered from crude oil distillation at the boiling point of fuels have customarily been further processed to produce fuel components or greater valuable chemical products or intermediates.

Conventional refinery systems generally combine multiple complex refinery units with petrochemical plants. For example, conventional refinery systems employ atmospheric and vacuum distillation of crude oil followed by hydrocracking units to produce naphtha, Liquefied Petroleum Gas (LPG), and other light fractions. Then, these materials are further processed in a steam cracker, a naphtha cracker, a reformer unit for benzene, toluene, and xylenes (BTX) production, a fluidized catalytic cracking unit, or a combination of these to produce petrochemical products, such as olefins.

SUMMARY

Despite conventional refinery systems for producing petrochemical products and intermediates from hydrocarbon feeds, these complex refinery systems are not readily convertible to shift production between different petrochemical products and intermediates, such as between different light olefins, based on market demand.

Accordingly, there is an ongoing need for systems and processes to convert hydrocarbon feeds to light olefins, such as ethylene, propylene, or both, where the systems and processes enable the selectivity of the process to either ethylene or propylene to be modified in response to changing product demand. These needs are met by embodiments of the systems and processes for converting hydrocarbon feeds to olefins described in the present disclosure. The processes of the present disclosure utilize steam catalytic cracking of hydrocarbon feeds in the presence of steam and a nano-zeolite cracking catalyst in either an ethylene-selective mode or a propylene-selective mode to produce a steam cracking effluent comprising light olefins, such as ethylene, propylene, or a combination of both. The systems and processes of the present disclosure utilize various steam catalyst cracking configurations and reaction settings to enable the selectivity of the process to either ethylene or propylene, while also accommodating a hydrocarbon feed blend to be used, such as a blend of light naphtha, light condensate gas shale, middle range naphtha, heavy range naphtha, bunker fuel, vacuum gas oils, or combinations of these. Accordingly, the systems and processes of the present disclosure enable selectivity of either ethylene or propylene within the same process. The systems and processes of the present disclosure may also enable increased flexibility in the blend of hydrocarbon feeds while maintaining selectivity for either ethylene or propylene.

According to one or more aspects of the present disclosure, a process for converting a hydrocarbon feed to produce light olefins, may comprise contacting the hydrocarbon feed with steam in the presence of a cracking catalyst in a steam catalytic cracking reactor at reaction conditions sufficient to cause at least a portion of the hydrocarbons in the hydrocarbon feed to undergo one or more cracking reactions to produce a steam catalytic cracking effluent comprising ethylene, propylene, or both, wherein the process is capable of being transitioned between an ethylene-selective mode and a propylene-selective mode. The process may further comprise determining whether to produce ethylene or propylene; when producing ethylene, then operating the process in ethylene-selective mode comprises producing more ethylene than propylene; or when producing propylene, then operating the process in propylene-selective mode comprises producing more propylene than ethylene.

In another aspect of the present disclosure, a process for upgrading a hydrocarbon feed, may comprise configuring a steam catalytic cracking reactor in either an ethylene-selective mode or a propylene-selective mode, where configuring the steam catalytic cracking reactor comprises selecting a configuration for the steam catalytic cracking reactor; selecting one or more settings for the steam catalytic cracking reactor; loading a cracking catalyst based on the one or more steam catalytic cracking reactor settings; loading an inert carrier pre-heating into the steam catalytic cracking reactor; adjusting a temperature for the steam catalytic cracking reactor based on the one or more steam catalytic cracking reactor settings; adjusting a liquid hourly volumetric space velocity for one or more feed pumps in the steam catalytic cracking reactor; and contacting the hydrocarbon feed with steam in the presence of the cracking catalyst in the steam catalytic cracking reactor at reaction conditions sufficient to cause at least a portion of the hydrocarbons in the hydrocarbon feed to undergo one or more cracking reactions to produce a steam catalytic cracking effluent comprising ethylene, propylene, or both.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
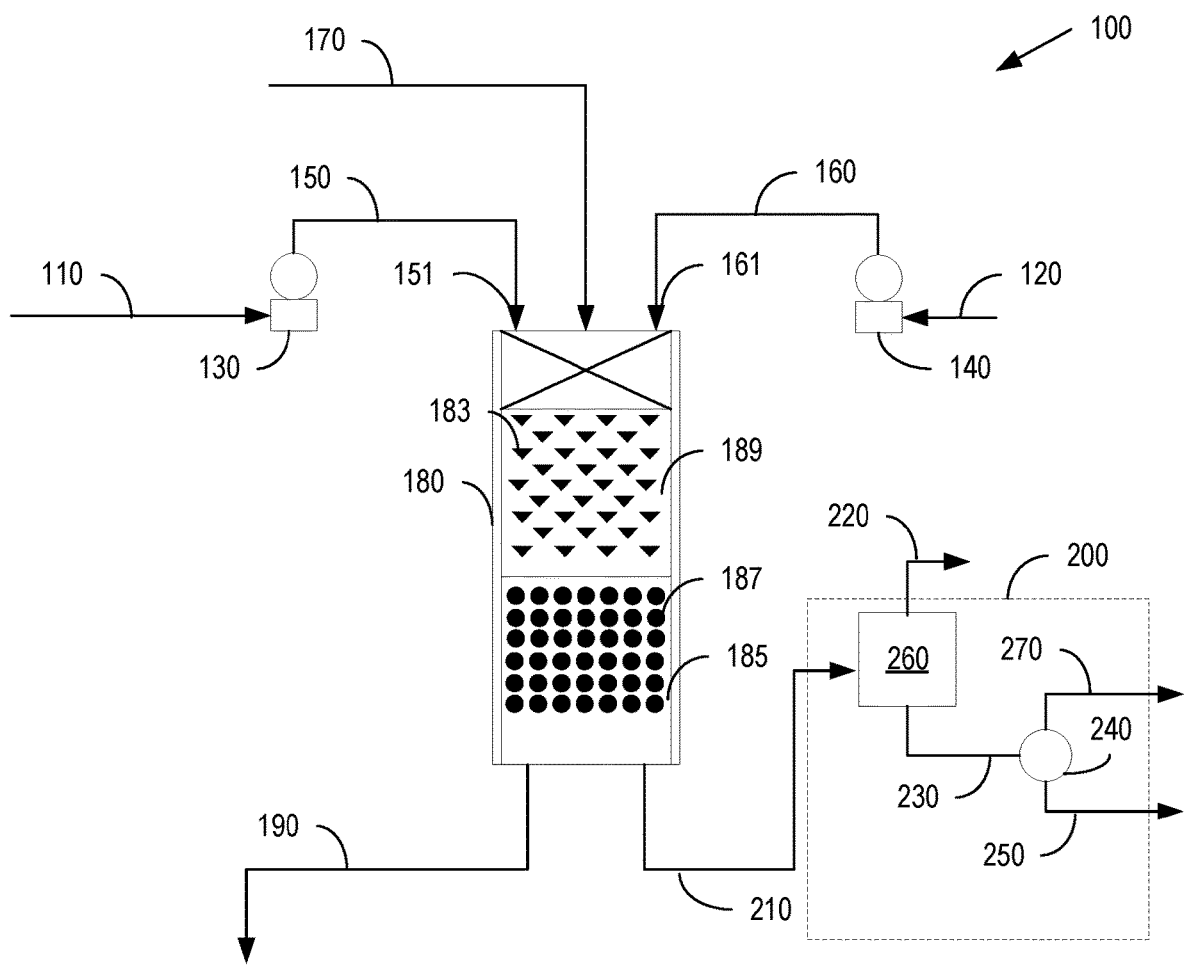
FIG. 1 schematically depicts a generalized flow diagram of a system for converting heavy hydrocarbon fees to light olefins, according to one or more embodiments shown and described in this disclosure.

For the purpose of describing the simplified schematic illustrations and descriptions of FIGS. 1-4, the numerous valves, temperature sensors, pressure sensors, electronic controllers, pumps, and the like that may be employed and well known to those of ordinary skill in the art of certain chemical processing operations are not included. Further, accompanying components that are often included in chemical processing operations, such as, for example, air supplies, heat exchangers, surge tanks, compressors, or other related systems may not be depicted. It would be known that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines, which may serve to transfer process steams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows, which do not connect two or more system components, signify a product stream, which exits the depicted system, or a system inlet stream, which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagram of FIG. 1. Mixing or combining may also include mixing by directly introducing both streams into the same reactor, separation device, or other system component. For example, it should be understood that when two streams are depicted as being combined directly prior to entering a separation unit or reactor, that, in embodiments, the streams could equivalently be introduced into the separation unit or reactor individually and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

The present disclosure is directed to systems and process for converting heavy hydrocarbon feeds, such as but not limited to crude oil, to produce more valuable products and chemical intermediates, such as light olefins. Referring to FIG. 1, one embodiment of a steam catalytic cracking system 100 for upgrading a hydrocarbon feed 110 comprising crude oil or other heavy oil is schematically depicted. The steam catalytic cracking system 100 may include at least one steam catalytic cracking reactor 180 and a cracking effluent separation system 200 disposed downstream of the steam catalytic cracking reactor 180. The steam catalytic cracking reactors 180 of the present disclosure may be switched between a propylene-selective mode and an ethylene-selective mode by switching catalyst reactor configurations and reaction settings. Thus, the steam catalytic cracking processes of the present disclosure may be easily adapted to produce different light olefin products in response to changes in market demand. Furthermore, the processes described in the present disclosure utilize refinery blends mixed with heavy feedstock to readily utilize surplus heavy feedstock while maintaining high yield of olefins.

Referring to FIG. 1, processes of the present disclosure for upgrading a hydrocarbon feed to produce light olefins include contacting the hydrocarbon feed 110 with steam in the presence of a cracking catalyst 187 at reaction condition sufficient to cause at least a portion of hydrocarbons in the hydrocarbon feed 110 to undergo one or more cracking reactions to produce a steam catalytic cracking effluent 210 comprising ethylene, propylene, or both, wherein the process is capable of being transitioned between an ethylene-selective mode and a propylene-selective mode. The process further includes determining whether to produce ethylene or propylene; when producing ethylene, then operating the process in the ethylene-selective mode, which produces a greater amount of ethylene compared to operating in the propylene-selective mode; or when producing propylene, then operating the process in the propylene-selective mode, which produces a greater amount of propylene compared to operating in the ethylene-selective mode.

In embodiments, the processes may include transitioning the steam catalytic cracking reactor 180 from the propylene-selective mode to the ethylene-selective mode by maintaining or adjusting a load volume of the cracking catalyst in the reaction zone so that a ratio of height to diameter of the reaction zone in the steam catalytic cracking reactor 180 is from 0.5 to 3.5. Transitioning the steam catalytic cracking reactor 180 from the propylene-selective mode to the ethylene-selective mode may also include adjusting the ratio of the inert carrier pre-heating loaded volume to the cracking catalyst loading volume into the range of from 0.1 to 6.

In embodiments, the process may include transitioning the steam catalytic cracking reactor 180 from the ethylene-selective mode to the propylene-selective mode by maintaining or adjusting a load volume of the cracking catalyst in the reaction zone so that the ratio of height to diameter of the reaction zone in the steam catalytic cracking reactor 180 is from 0.5 to 3.5. Transitioning the steam catalytic cracking reactor 180 from the ethylene-selective mode to the propylene-selective mode may also include adjusting the ratio of the inert carrier pre-heating loaded volume to the cracking catalyst loading volume in the range of from 0.1 to 4.

In embodiments, the process may include transitioning the steam catalytic cracking reactor 180 to a high-throughput propylene-selective mode by maintaining or adjusting a load volume of the cracking catalyst in the reaction zone so that the ratio of the height to diameter of the reaction zone in the steam catalytic cracking reactor 180 is from 4.5 to 8. Transitioning the steam catalytic cracking reactor 180 to the high-throughput propylene-selective mode may also include adjusting the ratio of the inert carrier pre-heating loaded volume to the cracking catalyst loading volume into a range of from 0.1 to 6.

Thus, the steam catalytic cracking system 100 of the present disclosure may be readily operated for either ethylene-selectivity or propylene-selectivity, including a high-throughput propylene-selective mode, and may be operated with a variety of hydrocarbon feed blends allowing greater flexibility for the system and process to adjust to market supply and demand, among other features.

As used in this disclosure, a "reactor" refers to any vessel, container, or the like, in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors, such as fixed bed reactors, and fluidized bed reactors. As used in the present disclosure, the term "fixed bed reactor" refers to a reactor in which a catalyst is confined within the reactor in a reaction zone in the reactor and is not circulated continuously through a reactor and regenerator system.

As used in this disclosure, one or more "reaction zones" may be disposed within a reactor. As used in this disclosure, a "reaction zone" refers to an area in which a particular reaction takes place in a reactor. For example, a packed bed reactor with multiple catalyst beds may have multiple reaction zones, in which each reaction zone is defined by the area of each catalyst bed.

As used in this disclosure, a "separation unit" refers to any separation device that at least partially separates one or more chemicals in a mixture from one another. For example, a separation unit may selectively separate different chemical species from one another, forming one or more chemical fractions. Examples of separation units include, without limitation, distillation columns, fractionators, flash drums, knock-out drums, knock-out pots, centrifuges, filtration devices, traps, scrubbers, expansion devices, membranes, solvent extraction devices, high-pressure separators, low-pressure separators, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided or separated into two or more process streams of desired composition.

As used in this disclosure, the terms "upstream" and "downstream" refer to the relative positioning of unit operations with respect to the direction of flow of the process streams. A first unit operation of a system is considered "upstream" of a second unit operation if process streams flowing through the system encounter the first unit operation before encountering the second unit operation. Likewise, a second unit operation is considered "downstream" of the first unit operation if the process streams flowing through the system encounter the first unit operation before encountering the second unit operation.

As used in the present disclosure, passing a stream or effluent from one unit "directly" to another unit refer to passing the stream or effluent from the first unit to the second unit without passing the stream or effluent through an intervening reaction system or separation system that substantially changes the composition of the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together also is not considered to comprise an intervening system that changes the composition of one or both of the streams or effluents being combined. Surge vessels are also not considered to be intervening systems that change the composition of a stream or effluent.

As used in this disclosure, the term "initial boiling point" or "IBP" of a composition refers to the temperature at which the constituents of the composition with the least boiling point temperatures begin to transition from the liquid phase to the vapor phase. As used in this disclosure, the term "end boiling point" or "EBP" of a composition refers to the temperature at which the greatest boiling temperature constituents of the composition transition from the liquid phase to the vapor phase. A hydrocarbon mixture can be characterized by a distillation profile expressed as boiling point temperatures at which a specific weight percentage of the composition has transitioned from the liquid phase to the vapor phase.

As used in this disclosure, the term "atmospheric boiling point temperature" refers to the boiling point temperature of a compound at atmospheric pressure.

As used in this disclosure, the term "effluent" refers to a stream that is passed out of a reactor, a reaction zone, or a separation unit following a particular reaction or separation. Generally, an effluent has a different composition than the stream that entered the separation unit, reactor, or reaction zone. It should be understood that when an effluent is passed to another system unit, only a portion of that system stream may be passed. For example, a slip stream or bleed stream may carry some of the effluent away, meaning that only a portion of the effluent may enter the downstream system unit. The term "reaction effluent" may more particularly be used to refer to a stream that is passed out of a reactor or reaction zone.

As used in this disclosure, the term "catalyst" refers to any substance that increases the rate of a specific chemical reaction. Catalysts described in this disclosure may be utilized to promote various reactions, such as, but not limited to, steam catalytic cracking. However, some catalysts described in the present disclosure may have multiple forms of catalytic activity, and calling a catalyst by one particular function does not render that catalyst incapable of being catalytically active for other functionality.

As used in this disclosure, the term "cracking" generally refers to a chemical reaction where a molecule having carbon-carbon bonds is broken into more than one molecule by the breaking of one or more of the carbon-carbon bonds or a cyclic molecule having carbon-carbon bonds is converted to a non-cyclic molecule by the breaking or one or more of the carbon-carbon bonds. As used in the present disclosure, the term "steam catalytic cracking" refers to cracking conducted in the presence of steam and a catalyst.

As used in this disclosure, the term "crude oil" or "whole crude oil" is to be understood to mean a mixture of petroleum liquids, gases, or combinations of liquids and gases, including, in embodiments, impurities such as but not limited to sulfur-containing compounds, nitrogen-containing compounds, and metal compounds, that have not undergone significant separation or reaction processes. Crude oils are distinguished from fractions of crude oil. In certain embodiments, the crude oil feedstock may be a minimally treated light crude oil to provide a crude oil feedstock having total metals (Ni+V) content of less than 5 parts per million by weight (ppmw) and Conradson carbon residue of less than 5 wt. %.

It should further be understood that streams may be named for the components of the stream, and the component for which the stream is named may be the major component of the stream (such as comprising from 50 wt. %, from 70 wt. %, from 90 wt. %, from 95 wt. %, from 99 wt. %, from 99.5 wt. %, or even from 99.9 wt. % of the contents of the stream to 100 wt. % of the contents of the stream, which does not include inert gases, unless otherwise indicated). It should also be understood that components of a stream are disclosed as passing from one system component to another when a stream comprising that component is disclosed as passing from that system component to another. For example, a disclosed "hydrocarbon stream" passing to a first system component or from a first system component to a second system component should be understood to equivalently disclose the "hydrocarbons" passing to the first system component or passing from a first system component to a second system component.

There is increasing demand for light olefins, such as ethylene and propylene, in the basic petrochemicals industry. Ethylene and propylene may be produced through steam cracking process from ethane gas, propane gas, butane, naphtha, and gas oil feedstock. Ethylene and propylene may be produced through steam cracking, however, steam cracking is generally unsuitable for upgrading heavy hydrocarbon feeds, such as crude oil or refinery heavy feed blends. Furthermore, different processes may be used to increase ethylene, such as catalytic pyrolysis process, or propylene production, such as propane dehydrogenation processes (PDH) and high severity fluidized catalytic cracking (HS-FCC). However, such processes have several limitations including high catalyst-to-oil ratios and limited olefin yield. Furthermore, such processes cannot be readily manipulated to switch between increased propylene and increased ethylene production.

The present disclosure is directed to steam catalytic cracking to convert heavy hydrocarbon feeds, such as crude oil or heavy feedstock blends, to valuable light olefins, such as ethylene and propylene, with flexibility to switch production from greater selectivity towards propylene to greater selectivity towards ethylene. As previously discussed, the steam catalytic cracking reactors may be switched between a propylene-selective mode and an ethylene-selective mode by switching catalyst configurations and reaction settings. Thus, the steam catalytic cracking processes may be easily converted between propylene selectivity and ethylene selectivity in response to changes in market demand. Furthermore, the processes described in the present disclosure utilize refinery blends mixed with heavy feedstock to readily utilize surplus heavy feedstock while maintaining high yield of olefins, such as ethylene, propylene, or both.

The systems and processes of the present disclosure utilize various steam catalytic cracking configurations and reaction settings within the same process to enable selectivity for either ethylene or propylene production. Accordingly, the systems and process of the present disclosure enable selectivity of increased yield and production of either ethylene or propylene within the same process. Referring to FIG. 1, the steam catalytic cracking system 100 may be readily operated for either ethylene-selectivity or propylene-selectivity, and may be operated with a variety of hydrocarbon feed blends allowing greater flexibility for the system and process to adjust to market supply and demand, among other features.

Referring now to FIG. 1, a process of the present disclosure for converting a hydrocarbon feed 110 to light olefins, includes contacting the hydrocarbon feed 110 with steam in the presence of a cracking catalyst 187 in at least one steam catalytic cracking reactor 180 at reaction conditions sufficient to cause at least a portion of hydrocarbons in the hydrocarbon feed 110 to undergo one or more cracking reactions to produce a steam catalytic cracking effluent 210 comprising light olefins.

The hydrocarbon feed 110 may include one or more heavy oils, such as but not limited to crude oil, bitumen, oil sand, shale oil, coal liquids, vacuum residue, tar sands, other heavy oil streams, or combinations of these. It should be understood that, as used in this disclosure, a "heavy oil" refers to a raw hydrocarbon, such as whole crude oil, which has not been previously processed through distillation, or may refer to a hydrocarbon oil, which has undergone some degree of processing prior to being introduced to the steam catalytic cracking system 100 as the hydrocarbon feed 110. The hydrocarbon feed 110 may have a density of greater than or equal to 0.80 grams per milliliter. The hydrocarbon feed 110 may have an end boiling point (EBP) of greater than 565° C. The hydrocarbon feed 110 may have a concentration of nitrogen of less than or equal to 3000 parts per million by weight (ppmw).

In embodiments, the hydrocarbon feed 110 may be a crude oil, such as whole crude oil, or synthetic crude oil. The crude oil may have an American Petroleum Institute (API) gravity of from 22 degrees to 50 degrees, such as from 22 degrees to 40 degrees, from 25 degrees to 50 degrees, or from 25 degrees to 40 degrees. In embodiments, the hydrocarbon feed 110 may include an extra light crude oil, a light crude oil, a heavy crude oil, or combinations of these. In embodiments, the hydrocarbon feed 110 can be a light crude oil, such as but not limited to an Arab light (AL) export crude oil. Example properties for an exemplary grade of AL export crude oil are provided in Table 1.

TABLE 1

Example of AL Export Feedstock

| Analysis | Units | Value | Test Method |
|---|---|---|---|
| American Petroleum Institute (API) gravity | degree | 33.13 | ASTM D287 |
| Density | grams per milliliter (g/mL) | 0.8595 | ASTM D287 |
| Carbon Content | weight percent (wt. %) | 85.29 | ASTM D5291 |
| Hydrogen Content | wt. % | 12.68 | ASTM D5292 |
| Sulfur Content | wt. % | 1.94 | ASTM D5453 |
| Nitrogen Content | parts per million by weight (ppmw) | 849 | ASTM D4629 |
| Asphaltenes | wt. % | 1.2 | ASTM D6560 |
| Micro Carbon Residue (MCR) | wt. % | 3.4 | ASTM D4530 |
| Vanadium (V) Content | ppmw | 15 | IP 501 |
| Nickel (Ni) Content | ppmw | 12 | IP 501 |
| Arsenic (As) Content | ppmw | 0.04 | IP 501 |
| Boiling Point Distribution | | | |
| Initial Boiling Point (IBP) | Degrees Celsius (° C.) | 33 | ASTM D7169 |
| 5% Boiling Point (BP) | ° C. | 92 | ASTM D7169 |
| 10% BP | ° C. | 133 | ASTM D7169 |
| 20% BP | ° C. | 192 | ASTM D7169 |
| 30% BP | ° C. | 251 | ASTM D7169 |
| 40% BP | ° C. | 310 | ASTM D7169 |
| 50% BP | ° C. | 369 | ASTM D7169 |
| 60% BP | ° C. | 432 | ASTM D7169 |
| 70% BP | ° C. | 503 | ASTM D7169 |
| 80% BP | ° C. | 592 | ASTM D7169 |
| 90% BP | ° C. | >720 | ASTM D7169 |
| 95% BP | ° C. | >720 | ASTM D7169 |
| End Boiling Point (EBP) | ° C. | >720 | ASTM D7169 |
| BP range C5-180° C. | wt. % | 18.0 | ASTM D7169 |
| BP range 180° C.-350° C. | wt. % | 28.8 | ASTM D7169 |
| BP range 350° C.-540° C. | wt. % | 27.4 | ASTM D7169 |
| BP range >540° C. | wt. % | 25.8 | ASTM D7169 |

Weight percentages in Table 1 are based on the total weight of the crude oil.

In embodiments, the hydrocarbon feed 110 may be an Arab Extra Light (AXL) crude oil. An example boiling point distribution for an exemplary grade of an AXL crude oil is provided in Table 2.

TABLE 2

Example of AXL Feedstock

| Property | Units | Value | Test Method |
|---|---|---|---|
| 0.1% Boiling Point (BP) | ° C. | 21 | ASTM D7169 |
| 5% BP | ° C. | 65 | ASTM D7169 |
| 10% BP | ° C. | 96 | ASTM D7169 |
| 15% BP | ° C. | 117 | ASTM D7169 |
| 20% BP | ° C. | 141 | ASTM D7169 |
| 25% BP | ° C. | 159 | ASTM D7169 |
| 30% BP | ° C. | 175 | ASTM D7169 |
| 35% BP | ° C. | 196 | ASTM D7169 |
| 40% BP | ° C. | 216 | ASTM D7169 |
| 45% BP | ° C. | 239 | ASTM D7169 |
| 50% BP | ° C. | 263 | ASTM D7169 |
| 55% BP | ° C. | 285 | ASTM D7169 |
| 60% BP | ° C. | 308 | ASTM D7169 |
| 65% BP | ° C. | 331 | ASTM D7169 |
| 70% BP | ° C. | 357 | ASTM D7169 |
| 75% BP | ° C. | 384 | ASTM D7169 |
| 80% BP | ° C. | 415 | ASTM D7169 |
| 85% BP | ° C. | 447 | ASTM D7169 |
| 90% BP | ° C. | 486 | ASTM D7169 |
| 95% BP | ° C. | 537 | ASTM D7169 |
| End Boiling Point (EBP) | ° C. | 618 | ASTM D7169 |

When the hydrocarbon feed 110 comprises a crude oil, the crude oil may be a whole crude or may be a crude oil that has undergone at some processing, such as desalting, solids separation, scrubbing. For example, the hydrocarbon feed 110 may be a de-salted crude oil that has been subjected to a de-salting process. In embodiments, the hydrocarbon feed 110 may include a crude oil that has not undergone pretreatment, separation (such as distillation), or other operation or process that changes the hydrocarbon composition of the crude oil prior to introducing the crude oil to the steam catalytic cracking system 100.

In embodiments, the hydrocarbon feed 110 can be a crude oil having a boiling point profile as described by the 5 wt. % boiling temperature, the 25 wt. % boiling temperature, the 50 wt. % boiling temperature, the 75 wt. % boiling temperature, and the 95 wt. % boiling temperature. These respective boiling temperatures correspond to the temperatures at which a given weight percentage of the hydrocarbon feed stream boils. In embodiments, the crude oil may have one or more of a 5 wt. % boiling temperature of less than or equal to 150° C.; a 25 wt. % boiling temperature of less than or equal to 225° C. or less than or equal to 200° C.; a 50 wt. % boiling temperature of less than or equal to 500° C., less than or equal 450° C., or less than or equal to 400° C.; a 75 wt. % boiling temperature of less than 600° C., less than or equal to 550° C.; a 95 wt. % boiling temperature of greater than or equal to 550° C. or greater than or equal to 600° C.; or combinations of these. In embodiments, the crude oil may have one or more of a 5 wt. % boiling temperature of from 0° C. to 100° C.; a 25 wt. % boiling temperature of from 150° C. to 250° C., a 50 wt. % boiling temperature of from 250° C. to 400° C., a 75 wt. % boiling temperature of from 350° C. to 600° C. and an end boiling point temperature of from 500° C. to 1000° C., such as from 500° C. to 800° C.

In embodiments, the hydrocarbon feed 110 may include one or more secondary hydrocarbon sources in addition to a crude oil. Secondary hydrocarbon sources may include light naphtha, middle range naphtha, heavy range naphtha, a whole range bunker fuel cut up to 620° C. light condensate gas shale, vacuum gas oil (VGO), or combinations thereof. In embodiments, the hydrocarbon feed 110 may include from 5 wt. % to 50 wt. % secondary hydrocarbon sources. In embodiments, the total hydrocarbon feed 110 to the steam catalytic cracking system 100 may include from 10 wt. % to 50 wt. %, from 15 wt. % to 50 wt. %, from 20 wt. % to 50 wt. %, from 5 wt. % to 45 wt. %, from 5 wt. % to 40 wt. %, from 10 wt. % to 45 wt. %, from 10 wt. % to 40 wt. %, from 15 wt. % to 45 wt. %, or from 15 wt. % to 40 wt. % secondary hydrocarbon sources with the balance being crude oil.

Referring again to FIG. 1, one embodiment of a steam catalytic cracking system 100 for steam catalytic cracking a hydrocarbon feed 110 is schematically depicted. It should be understood that other configurations of the steam catalytic cracking system may be suitable for incorporation into the steam catalytic cracking system 100 for converting hydrocarbon feeds to olefins. The steam catalytic cracking system 100 may include at least one steam catalytic cracking reactor 180. The steam catalytic cracking reactor 180 may include one or more fixed bed reactors. In embodiments, the steam catalytic cracking reactor 180 may include a plurality of fixed bed reactors operated in a swing mode.

Referring again to FIG. 1, the hydrocarbon feed 110 may be introduced to the steam catalytic cracking reactor 180. In embodiments, the hydrocarbon feed 110 may be introduced directly to the steam catalytic cracking system 100, such as by passing the crude oil of the hydrocarbon feed 110 to the steam catalytic cracking reactor 180 without passing the hydrocarbon feed 110 to any separation system or unit operation that changes the hydrocarbon composition of the hydrocarbon feed 110. In embodiments, the hydrocarbon feed 110 may be processed upstream of the steam catalytic cracking system 100 to remove contaminants, such as but not limited to nitrogen compounds, sulfur-containing compounds, heavy metals, other contaminants, or combinations of these that may reduce the effectiveness of the cracking catalyst.

The processes disclosed herein can include introducing the hydrocarbon feed 110 to the steam catalytic cracking system 100, such as introducing the hydrocarbon feed 110 to the steam catalytic cracking reactor 180. Introducing the hydrocarbon feed 110 to the steam catalytic cracking reactor 180 may include heating the hydrocarbon feed 110 to a temperature of from 35° C. to 150° C. and then passing the hydrocarbon feed 110 to the steam catalytic cracking reactor 180. In embodiments, the hydrocarbon feed 110 may be heated from 40° C. to 150° C., from 45° C. to 150° C., from 50° C. to 150° C., from 35° C. to 145° C., from 40° C. to 145° C., from 45° C. to 145° C., from 35° C. to 140° C., from 40° C. to 140° C., or from 45° C. to 140° C.

In embodiments, passing the hydrocarbon feed 110 to the steam catalytic cracking reactor 180 may include passing the hydrocarbon feed 110 to a feed pump 130, where the feed pump 130 may increase the pressure of the hydrocarbon feed 110 and convey the hydrocarbon feed 110 to the steam catalytic cracking reactor 180. The flowrate of the feed pump 130 may be adjusted so that the hydrocarbon feed 110 is injected into the steam catalytic cracking reactor 180 at a liquid hourly space velocity of greater than or equal to 0.05 per hour ($h^{-1}$), greater than or equal to 0.03 $h^{-1}$, or greater than or equal to 1 $h^{-1}$. The hydrocarbon feed 110 may be injected into the steam catalytic cracking reactor 180 at a liquid hourly space velocity of less than or equal to 5 $h^{-1}$, less than or equal to 4 $h^{-1}$, less than or equal to 3 $h^{-1}$, less than or equal to 1.5 $h^{-1}$, less than or equal to 1 $h^{-1}$, or less than or equal to 0.8 $h^{-1}$. The hydrocarbon feed 110 may be injected into the steam catalytic cracking reactor 180 at a liquid hourly space velocity of from 0.05 $h^{-1}$ to 5 $h^{-1}$, from 0.05 $h^{-1}$ to 4 $h^{-1}$, from 0.05 $h^{-1}$ to 3 $h^{-1}$, from 0.05 $h^{-1}$ to 1.5 $h^{-1}$, from 0.05 $h^{-1}$ to 1 $h^{-1}$, from 0.05 $h^{-1}$ to 0.8 $h^{-1}$, from 0.3 $h^{-1}$ to 5 $h^{-1}$, from 0.3 $h^{-1}$ to 4 $h^{-1}$, from 0.3 $h^{-1}$ to 3 $h^{-1}$, from 0.3 $h^{-1}$ to 1.5 $h^{-1}$, from 0.3 $h^{-1}$ to 1 $h^{-1}$, from 0.3 $h^{-1}$ to 0.8 $h^{-1}$, from 1 $h^{-1}$ to 5 $h^{-1}$, from 1 $h^{-1}$ to 3 $h^{-1}$, from 1 $h^{-1}$ to 1.5 $h^{-1}$ via feed inlet line 150. The hydrocarbon feed 110 may be further pre-heated in the feed inlet line 150 to a temperature of from 100° C. to 250° C. before injecting the hydrocarbon feed 110 into the steam catalytic cracking reactor 180.

Water 120 may be injected to the steam catalytic cracking reactor 180 through water line 160 via the water pump 140. The water line 160 may be pre-heated to heat the water 120 to a temperature of from 50° C. to 175° C., from 50° C. to 150° C., from 60° C. to 175° C., or from 60° C. to 170° C. The water 120 may be converted to steam in water line 160 or upon contact with the hydrocarbon feed 110 in the steam catalytic cracking reactor 180. The flowrate of the water pump 140 may be adjusted to deliver the water 120 (liquid, steam, or both) to the steam catalytic cracking reactor 180 at a gas hourly space velocity of greater than or equal to 0.1 $h^{-1}$, greater than or equal to 0.5 $h^{-1}$, greater than or equal to 1 $h^{-1}$, greater than or equal to 5 $h^{-1}$, greater than or equal to 6 $h^{-1}$, greater than or equal to 10 $h^{-1}$, or even greater than or equal to 15 $h^{-1}$. The water 120 may be introduced to the steam catalytic cracking reactor 180 at a gas hourly space velocity of less than or equal to 100 $h^{-1}$, less than or equal to 75 $h^{-1}$, less than or equal to 50 $h^{-1}$, less than or equal to 30 $h^{-1}$, or less than or equal to 20 $h^{-1}$. The water 120 may be introduced to the steam catalytic cracking reactor 180 at a gas hourly space velocity of from 0.1 $h^{-1}$ to 100 $h^{-1}$, from 0.1 $h^{-1}$ to 75 $h^{-1}$, from 0.1 $h^{-1}$ to 50 $h^{-1}$, from 0.1 $h^{-1}$ to 30 $h^{-1}$, from 0.1 $h^{-1}$ to 20 $h^{-1}$, from 1 $h^{-1}$ to 100 $h^{-1}$, from 1 $h^{-1}$ to 75 $h^{-1}$, from 1 $h^{-1}$ to 50 $h^{-1}$, from 1 $h^{-1}$ to 30 $h^{-1}$, or from 1 $h^{-1}$ to 20 $h^{-1}$.

The steam from injection of the water 120 into the steam catalytic cracking reactor 180 may reduce the hydrocarbon partial pressure, which may have the dual effects of increasing yields of light olefins (e.g., ethylene, propylene and butylene) as well as reducing coke formation on the cracking catalyst. Not intending to be limited by any particular theory, it is believed that light olefins like propylene and butenes are mainly generated from catalytic cracking reactions following the carbonium ion mechanism, and as these are intermediate products, they can undergo secondary reactions such as hydrogen transfer and aromatization (leading to coke formation). The steam may increase the yield of light olefins by suppressing these secondary bi-molecular reactions, and may reduce the concentration of reactants and products, which favor selectivity towards light olefins. The steam may also suppresses secondary reactions that are responsible for coke formation on catalyst surface, which is good for catalysts to maintain high average activation. These factors may show that a large steam-to-oil weight ratio may be beneficial to the production of light olefins.

As previously discussed, the steam catalytic cracking system 100 may contact the hydrocarbon feed 110 with steam in the presence of the nano-zeolite cracking catalyst to steam catalytically crack at least a portion of the hydrocarbons in the hydrocarbon feed 110 to produce olefins, such as but not limited to ethylene, propylene, butenes, or combinations of these. The steam catalytic cracking effluent 210 may exit the steam catalytic cracking system 100 and be passed through a heat exchanger (not shown) where a process fluid, such as water or pyrolysis fuel oil, cools the steam catalytic cracking effluent 210. The steam catalytic cracking effluent 210 may include olefins, such as but not limited to ethylene, propylene, butenes, or combinations of these. The steam catalytic cracking effluent 210 may be passed out of the steam catalytic cracking system 100 to one or more downstream operations, such as process operations for separating the steam catalytic cracking effluent 210 into one or more olefin product streams.

Referring again to FIG. 1, the steam catalytic cracking system 100 may be operable to contact the hydrocarbon feed 110 with steam (from water 120) in the presence of the cracking catalyst in the steam catalytic cracking reactor 180 under reaction conditions sufficient to cause at least a portion of the hydrocarbons from the hydrocarbon feed 110 to undergo one or more cracking reactions to produce a steam catalytic cracking effluent 210 comprising light olefins. In embodiments, the steam catalytic cracking effluent 210 may comprise light olefins, which may include but are not limited to ethylene, propylene, butenes, or combinations of these.

The steam catalytic cracking reactor 180 may be operated at a temperature of greater than or equal to 540° C., greater than or equal to 620° C., or greater than or equal to 690° C. The steam catalytic cracking reactor 180 may be operated at a temperature of less than or equal to 800° C., less than or equal to 790° C., less than or equal to 690° C., or even less than or equal to 675° C. The steam catalytic cracking reactor 180 may be operated at a temperature of from 540° C. to 790° C., from 540° C. to 690° C., from 540° C. to 675° C., from 540° C. to 620° C., from 540° C. to 615° C., from 570° C. to 615° C., from 570° C. to 620° C., from 570° C. to 750° C., from 620° C. to 790° C., from 620° C. to 690° C., from 630° C. to 675° C., from 600° C. to 690° C., or from 600° C. to 790° C. In embodiments, the steam catalytic cracking reactor 180 may be operated at a temperature of from 620° C. to 690° C., such as from 630° C. to 675° C. In embodiments, the steam catalytic cracking reactor 180 may be operated at a temperature of from 540° C. to 620° C., such as from 570° C. to 615° C. In embodiments, the steam catalytic cracking reactor 180 may be operated at a pressure of from 100 kPa to 200 kPa. In embodiments, the process may operate at atmospheric pressure (approximately 101 kilopascals).

The methods of the present disclosure may include contacting the hydrocarbon feed 110 with the steam (water 120) in the presence of the cracking catalyst 187 in the steam catalytic cracking reactor 180 for a residence time sufficient to convert at least a portion of the hydrocarbon compounds in the hydrocarbon feed 110 to light olefins. In embodiments, the methods may include contacting the hydrocarbon feed 110 with the steam (water 120) in the presence of the cracking catalyst 187 in the steam catalytic cracking reactor 180 for a residence time of from 1 second to 60 seconds, such as from 1 second to 30 seconds, from 1 second to 10 seconds, or about 10 seconds.

The cracking catalyst 187 may be a nano-zeolite cracking catalyst comprising nano-zeolite particles. A variety of nano-zeolites may be suitable for the steam catalytic cracking reactions in the steam catalytic cracking reactor 180. The nano-zeolite cracking catalyst may include a structured zeolite, such as an MFI, BEA, Y, or mordenite structured zeolite, for example. In embodiments, the nano-zeolite cracking catalyst may comprise nano ZSM-5 zeolite, nano BEA zeolite, nano Y-zeolite, nano mordenite zeolite, or combinations of these. In embodiments, the nano-zeolite cracking catalyst may include a combination of nano ZSM-5 zeolite and nano BEA zeolite. In embodiments, the nano-zeolite cracking catalyst may include a combination of nano ZSM-5 zeolite and nano Y-zeolite. In embodiments, the nano-zeolite cracking catalyst may include a combination of nano ZSM-5 zeolite and nano mordenite zeolite. The nano-zeolites, such as nano-ZSM-5, BEA, Y, or mordenite zeolite, or combinations of these may be in hydrogen form. In hydrogen form, the Brønsted acid sites in the zeolite, also known as bridging $O_H$—H groups, may form hydrogen bonds with other framework oxygen atoms in the zeolite framework.

The nano ZSM-5 zeolite, nano BEA zeolite, nano Y-zeolite, nano mordenite zeolite, or combinations of these, may have a molar ratio of silica to alumina to provide sufficient acidity to the nano-zeolite cracking catalyst to conduct the steam catalytic cracking reactions. The nano ZSM-5 zeolite, nano BEA zeolite, nano Y-zeolite, nano mordenite zeolite, or combinations of these, may have a molar ratio of silica to alumina of from 1 to 1000. The nano ZSM-5 zeolite, nano BEA zeolite, nano Y-zeolite, nano mordenite zeolite, or combinations of these, may have total acidity in the range of 0.2 to 2.5 mmol/g, 0.3 to 2.5 mmol/g, 0.4 to 2.5 mmol/g, 0.5 to 2.5 mmol/g, 0.2 to 2.0 mmol/g, 0.3 to 2.0 mmol/g, 0.4 to 2.0 mmol/g, or 0.5 to 2.0 mmol/g. The nano ZSM-5 zeolite, nano BEA zeolite, nano Y-zeolite, nano mordenite zeolite, or combinations of these, may contain Brønsted acid sites in the range of 0.1 to 1.0 mmol/g, 0.2 to 1.0 mmol/g, 0.3 to 1.0 mmol/g, 0.1 to 0.9 mmol/g, 0.2 to 0.9 mmol/g, or 0.3 to 0.9 mmol/g. The concentration of Brønsted acid sites may be determined by Pyridine Fourier-transform infrared spectroscopy (FTIR). Pyridine molecule was used as a probe molecule and introduced to the cell to saturate the sample and was evacuated at 150° C. The obtained peaks at approximately 1540 and 1450 $cm^{-1}$ represented Brønsted and Lewis acid sites respectively. The nano ZSM-5 zeolite, nano BEA zeolite, nano Y-zeolite, nano mordenite zeolite, or combinations of these, may have an average crystal size of from 0.1 nanometer (nm) to 900 nm, from 100 nm to 900 nm, from 200 nm to 900 nm, or from 0.1 nm to 300 nm. The average crystal size is determined by scanning electron microscopy (SEM) according to known methods.

The nano-zeolite cracking catalyst may also include an alumina binder, which may be used to consolidate the nanoparticles of nano ZSM-5 zeolite, nano BEA zeolite, nano Y-zeolite, nano mordenite zeolite, or combinations of these, to form the nano-zeolite cracking catalyst. The nano-zeolite cracking catalyst may be prepared by combining the nano ZSM-5 zeolite, nano BEA zeolite, nano Y-zeolite, nano mordenite zeolite, or combinations of these, with the aluminum binder and extruding the nano-zeolite cracking catalyst to form pellets or other catalyst shapes. The nano-zeolite cracking catalyst may include from 10 wt. % to 90 wt. %, from 10 wt. % to 50 wt. %, from 10 wt. % to 70 wt. %, from 30 wt. % to 70 wt. %, or from 30 wt. % to 50 wt. % alumina binder based on the total weight of the nano-zeolite cracking catalyst. The nano-zeolite cracking catalyst may have a mesoporous to microporous volume ratio in the range of from 0.5 to 1.5, from 0.6 to 1.5, from 0.7 to 1.5, from 0.5 to 1.0, from 0.6 to 1.0, or from 0.7 to 1.0.

The steam catalytic cracking reactor 180 may include a porous packing material 183, such as silica carbide packing, in an inert carrier pre-heating zone 189, which is disposed upstream of the steam cracking catalyst zone 185. The porous packing material 183 may be shaped in spheres, cylinders, or trilobe, quadlobe rings, other type of porous packing material, or combination of these packing materials. The porous packing material 183 may have a high void fraction, such as a void fraction of greater than or equal to 50%, greater than or equal to 55%, or in a range of from 55% to 65%. The porous packing material 183 may ensure efficient heat transfer to the hydrocarbon feed 110 and steam prior to conducting the steam catalytic cracking reaction in the steam cracking catalyst zone 185. The porous packing material 183 may enhance the heat transfer of the hydrocarbon feed 110 and steam by increasing uniform heat distribution throughout the inert carrier pre-heating zone 189. Further, the porous packing material 183 may enhance heat transfer radially throughout the inert carrier pre-heating zone 189.

Thus, the porous packing material 183 may be arranged in the inert carrier pre-heating zone 189 to achieve reaction temperature prior to reaching the steam cracking catalyst zone 185. Further, the volume of the porous packing material 183 loaded in the inert carrier pre-heating zone 189 and, thus, the volume of the inert carrier pre-heating zone 189 may be based on the selected reactor configuration, such as the reactor configuration for operating in an ethylene-selective mode, the reactor configuration for operating in a propylene-selective mode, or the reactor configuration for operating in the high-throughput propylene-selective mode. In embodiments, the porous packing material 183 may be loaded relative to the loaded catalyst (nano-zeolite cracking catalyst 187) in a ratio of porous packing material to catalyst of from 0.1 to 6, such as from 2 to 3. In embodiments, the porous packing material 183 may be loaded relative to the loaded catalyst (nano-zeolite cracking catalyst 187) in a ratio of porous packing material to catalyst of from 0.1 to 3, such as from 1 to 2. In embodiments, the porous packing material 183 may be loaded relative to the loaded catalyst (nano-zeolite cracking catalyst 187) in a ratio of porous packing material to catalyst of from 0.1 to 6, such as from 1 to 3.

The inert carrier pre-heating zone 189 may be operated at a temperature of from 540° C. to 790° C., from 540° C. to 690° C., from 540° C. to 675° C., from 540° C. to 620° C., from 540° C. to 615° C., from 570° C. to 615° C., from 570° C. to 620° C., from 570° C. to 790° C., from 620° C. to 790° C., from 620° C. to 690° C., from 630° C. to 675° C., from 600° C. to 690° C., or from 600° C. to 790° C. In embodiments, the inert carrier pre-heating zone 189 may be operated at a temperature of from 620° C. to 690° C., such as from 630° C. to 675° C. In embodiments, the inert carrier pre-heating zone 189 may be operated at a temperature of from 540° C. to 620° C., such as from 570° C. to 615° C. The difference in operating temperature between the inert carrier pre-heating zone 189 and the steam cracking catalyst zone 185 may be from 1° C. to 15° C.

The hydrocarbon feed 110 and steam enter via lines 150 and 160, respectively, into the steam catalytic cracking reactor 180 and pass through inlet feed distributor 151 and inlet feed distributor 161, respectively, at the top of the down-flow reactor. The inlet feed distributors 151 and 161 may distribute the hydrocarbon feed 110 and steam across the cross-sectional area of the steam catalytic cracking reactor 180 and may cause mixing of the hydrocarbon feed 110 and steam to produce a mixture. The mixture then flows into the inert carrier pre-heating zone 189 to further induce mixing between the heated hydrocarbon feed and steam before the mixture flows into the steam cracking catalyst zone 185.

Referring again to FIG. 1, the steam catalytic cracking effluent 210 may pass out of the steam catalytic cracking reactor 180. The steam catalytic cracking effluent 210 may include one or more products and intermediates, such as but not limited to, light hydrocarbon gases, olefins, aromatic compounds, pyrolysis oil, or combinations of these. Olefins in the steam catalytic cracking effluent 210 may include ethylene, propylene, butenes, or combinations of these. The olefins may be passed out of the steam catalytic cracking system 100 in the gaseous effluent 220, including olefins such as ethylene, propylene, butenes, or combinations of these; light hydrocarbon gases, such as methane, ethane, propane, n-butane, i-butane, or combinations of these; other gases, such as but not limited to hydrogen; or combinations of these. The gaseous effluent 220 may include the $C_2$-$C_4$ olefin products, such as but not limited to, ethylene, propylene, butenes (1-butene, cis-2-butene, trans-2-butene, isobutene, or combinations of these), or combinations of these, produced in the steam catalytic cracking reactor 180. The gaseous effluent 220 may include at least 90%, at least 95%, at least 98%, at least 99%, or at least 99.5% of the $C_2$-$C_4$ olefins from the steam catalytic cracking effluent 210. The gaseous effluent 220 may be passed to one or more downstream processes for further separation into one or more product streams. The steam catalytic cracking system 100 may also produce the liquid hydrocarbon effluent 270 and the aqueous effluent 250.

The steam catalytic cracking reactor 180 may be operated in a semi-continuous manner. In embodiments, during a conversion cycle, the steam catalytic cracking reactor 180 may be operated with the hydrocarbon feed 110 and water 120 flowing to the steam catalytic cracking reactor 180 for a period of time, at which point the nano-zeolite cracking catalyst 187 may be regenerated. Each conversion cycle of the steam catalytic cracking reactor 180 may be from 2 to 24 hours, from 2 to 20 hours, from 2 to 16 hours, from 2 to 12 hours, from 2 to 10 hours, from 2 to 8 hours, from 4 to 24 hours, from 4 to 20 hours, from 4 to 16 hours, from 4 to 12 hours, from 4 to 10 hours, or from 4 to 8 hours before switching off the feed pump 130 and the water pump 140. At the end of the conversion cycle, the flow of hydrocarbon feed 110 and water 120 may be stopped and the nano-zeolite cracking catalyst 187 may be regenerated during a regeneration cycle. In embodiments, the steam catalytic cracking system 100 may include a plurality of steam catalytic cracking reactors 180, which can be operated in parallel or in series. With a plurality of steam catalytic cracking reactors 180 operating in parallel, one or more of the steam catalytic cracking reactors 180 can continue in a conversion cycle while one or more of the other steam catalytic cracking reactors 180 are taken off-line for regeneration of the nano-zeolite cracking catalyst, thus maintaining continuous operation of the steam catalytic cracking system 100.

Referring again to FIG. 1, during a regeneration cycle, the steam catalytic cracking reactor 180 may be operated to regenerate the nano-zeolite cracking catalyst 187. The nano-zeolite cracking catalyst 187 may be regenerated to remove coke deposits accumulated during the conversion cycle. To regenerate the nano-zeolite cracking catalyst 187, hydrocarbon gas and liquid products produced by the steam catalytic cracking process may be evacuated from the steam catalytic cracking reactor 180.

Following evacuation of the hydrocarbon gases and liquids, air may be introduced to the steam catalytic cracking reactor 180 through gas line 170 at a gas hourly space velocity of from 10 $h^{-1}$ to 100 $h^{-1}$. The air pump flowing air through gas line 170 may operate at a temperature of from 10° C. to 55° C., at atmospheric pressure (approximately from 1 to 2 bar) with the flow pressure of from 5 pounds per square inch (PSI) to 100 PSI. The air may be passed out of the steam catalytic cracking reactor 180 through outlet line 190. While passing air through the nano-zeolite cracking catalyst 187 in the steam catalytic cracking reactor 180, the temperature of the steam catalytic cracking reactor 180 may be increased from the reaction temperature to a regeneration temperature of from 600° C. to 750° C. for a period of from 2 hours to 6 hours. The gas produced by air regeneration of nano-zeolite cracking catalyst 187 may be passed out of the steam catalytic cracking reactor 180 through outlet line 190 and may be analyzed by an in-line gas analyzer connected via outlet line 190 to detect the presence or concentration of carbon dioxide produced through decoking of the nano-zeolite cracking catalyst. Once the carbon dioxide concentration in the gases passing out of the steam catalytic cracking reactor 180 are reduced to less than 0.05% to 0.2% by weight, as determined by the in-line gas analyzer, the temperature of the steam catalytic cracking reactor 180 may be decreased from the regeneration temperature back to the reaction temperature. The air flow through gas line 170 may be stopped by closing gas line 170. After closing gas line 170, the steam catalytic cracking reactor system may be operated in either an ethylene-selective mode or a propylene-selective mode. After selecting an operation mode and appropriate steam catalytic cracking reactor configuration, the flow of the hydrocarbon feed 110 and water 120 may be resumed to begin another conversion cycle of steam catalytic cracking reactor 180.

As previously discussed, the relative demands of ethylene and propylene are constantly changing. Many conventional reactor systems for producing light olefins, such as ethylene and propylene, are designed to operate continuously in a single operating mode, with only small changes to operating parameters being possible. Thus, existing reaction system are not easily changed to adapt to changing market demands.

The steam catalytic cracking reaction system of the present disclosure can be operated in at least three different operating modes and two reactor configuration, which enable the steam catalytic cracking reaction systems to adapt operations to meet changing market demands for ethylene and propylene. In particular, the steam catalytic cracking reaction system can have a first reactor configuration with a first volume of cracking catalyst and a second reactor configuration with a second volume of cracking catalyst. When configured in the first reactor configuration, the steam catalytic cracking reaction system can operate in two different operating modes: an ethylene-selective mode and a propylene-selective mode. In the ethylene-selective mode, the selectivity of the steam catalytic cracking reaction towards ethylene is increased, and in the propylene-selective mode, the selectivity of the steam catalytic cracking reaction to propylene is increased. When configured in the second reactor configuration, the steam catalytic cracking reactor may be operated in a third operating mode, which is a high-throughput propylene-selective mode (i.e., high production rate propylene-selective mode). Each of the reactor configurations and operating modes will now be described in further detail.

Figure 2:
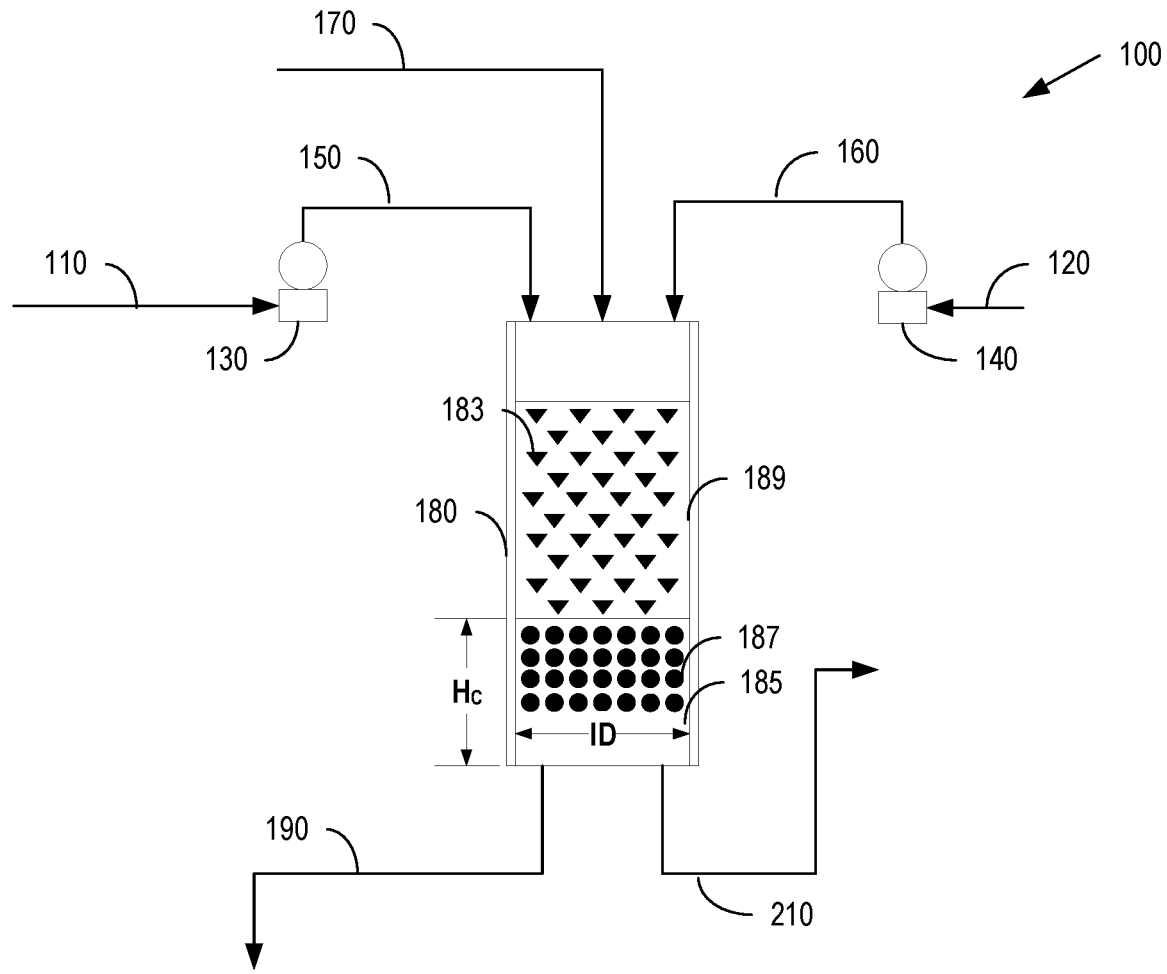
FIG. 2 schematically depicts a first configuration of a steam catalytic cracking reactor of the system of FIG. 1, according to one or more embodiments shown and described in this disclosure.

Referring now to FIG. 2, the steam catalytic cracking system 100 may be configured according to the first reactor configuration. In the first reactor configuration, the cracking catalyst 187 may be loaded into the steam cracking catalyst zone 185 of the steam catalytic cracking reactor 180 in an amount that results in the steam cracking catalyst zone 185 having a ratio of height $H_C$ to inside diameter ID of from 0.5 to 3.5, such as from 0.5 to 3, from 0.5 to 2.5, from 0.5 to 2, from 1 to 3.5, from 1 to 3, from 1 to 2.5, from 1 to 2, from 1.5 to 3.5, from 1.5 to 3, from 1.5 to 2.5, from 1.5 to 2, from 2 to 3.5, from 2 to 3, from 2 to 2.5, from 2.5 to 3.5, from 2.5 to 3, or about 2. The height $H_C$ is the distance from the top of the steam cracking catalyst zone 185 to the bottom of the steam cracking catalyst zone 185. The inside diameter ID is the inner diameter of the steam cracking catalyst zone 185. The cracking catalyst 187 may be any of the cracking catalysts described in the present disclosure as being suitable for the steam catalytic cracking reactor. The volume of the cracking catalyst 187 loaded into the steam cracking catalyst zone 185 may have a height of from 3 units to 5 units, such as about 4 units. A unit may be defined as a centimeter, meter, inch, foot, or yard. The loaded cracking catalyst 187 may be loaded into the steam cracking catalyst zone 185 with diameter of from 0.5 to 3 units, such as about 2 units. The loaded cracking catalyst 187 may be loaded into the cracking reactor zone 185 with a volume of from 0.59 to 35.34 cubic units, such as about 12.57 cubic units. Once the cracking catalyst 187 is loaded into the steam catalytic cracking reactor 180, the porous packing material 183 may be loaded on top of the cracking catalyst 187. In embodiments, the volume of porous packing material 183 may be sufficient to fill the remaining internal volume of the steam catalytic cracking reactor 180 up to the inlet feed distributors 151 and 161.

When in the first reactor configuration, the steam catalytic cracking reactor 180 may be operated in two operating modes: an ethylene-selective mode and a propylene-selective mode. In response to greater market demand for ethylene, the steam catalytic cracking reactor 180 may be configured in the first reactor configuration and operated in the ethylene-selective operating mode. In the ethylene-selective operating mode, the steam catalytic cracking reactor 180 may produce a greater proportion of ethylene. The steam catalytic cracking system 100 may be transitioned to the ethylene-selective mode in response to increasing market demand for ethylene. In the ethylene-selective operating mode, the steam catalytic cracking reactor 180 may be in the first reactor configuration in which the volume of the cracking catalyst charged to the steam catalytic cracking reactor 180 is such that the steam cracking catalyst zone 185 has a ratio of height $H_C$ to inside diameter ID of from 0.5 to 3.5. In the ethylene-selective operating mode, the steam catalytic cracking reactor 180 may be operated at a greater temperature and a greater flow rate of the hydrocarbon feed 110 to the steam catalytic cracking reactor 180 compared to the propylene-selective operating mode.

In the ethylene-selective operating mode, the hydrocarbon feed 110 may be introduced to the steam catalytic cracking reactor 180. The hydrocarbon feed 110 may have any of the compositions previously discussed in the present disclosure. In embodiments, the hydrocarbon feed 110 may include crude oil and from 5 wt. % to 50 wt. % of one or more of straight run naphtha, light naphtha, middle range naphtha, heavy range naphtha, whole range bunker fuel cut up to 620° C., light condensate gas shale, vacuum gas oil (VGO), or combinations of these. The hydrocarbon feed 110 may be heated to a temperature of from 20° C. to 85° C. and then introduced to a feed pump 130. In the ethylene-selective operating mode, the hydrocarbon feed 110 is injected into the steam catalytic cracking reactor 180 at a liquid hourly space velocity of from 0.05 $h^{-1}$ 5 $h^{-1}$, such as at a liquid hourly space velocity of from 0.3 $h^{-1}$ to 5 $h^{-1}$, from 0.3 $h^{-1}$ to 1.5 $h^{-1}$, 0.8 $h^{-1}$ to 5 $h^{-1}$, from 0.8 $h^{-1}$ to 1.5 $h^{-1}$, from 1 $h^{-1}$ to 5 $h^{-1}$, or from 1 $h^{-1}$ to 1.5 $h^{-1}$. The hydrocarbon feed 110 may be further pre-heated in feed inlet line 150 to a temperature between 70° C. to 150° C. before injecting the hydrocarbon feed 110 into the steam catalytic cracking reactor 180.

Water 120 may injected into the steam catalytic cracking reactor 180 through water line 160 via the water pump 140. The water 120 may be pre-heated at a temperature of from 10° C. to 55° C. The water line 160 may be pre-heated to a temperature of from 70° C. to 150° C. The water may be converted to steam in water line 160 or upon contact with the hydrocarbon feed 110 in the steam catalytic cracking reactor 180. The flow rate of the water pump 130 may be adjusted so that the water 120 is injected into the steam catalytic cracking reactor 180 at a liquid hourly space velocity of 0.5 $h^{-1}$ to 50 $h^{-1}$, such as from 1 $h^{-1}$ to 10 $h^{-1}$.

The hydrocarbon feed 110 and the water 120 are injected into the steam catalytic cracking reactor 180. The water 120 and hydrocarbon feed 110 may flow into the steam catalytic cracking reactor in a ratio of water to hydrocarbon of from 50 to 1, such as from 5 to 1. The hydrocarbon feed and the water may mix before being superheated in the inert carrier pre-heating zone 189 to a temperature of from 90° C. to 250° C. to further induce mixing. The inert carrier pre-heating zone 189 may be loaded with porous packing material 183, such as silica carbide. The porous packing material 183 may be loaded relative to the loaded cracking catalyst (nano-zeolite cracking catalyst 187) in a ratio of porous packing material to catalyst of from 0.1 to 6, such as from 2 to 3.

The superheated hydrocarbon feed and steam mixture then flows into the steam cracking catalyst zone 185. In the ethylene-selective operating mode, the steam cracking catalyst zone 185 may be operated at a temperature of from 620° C. to 690° C., such as from 630° C. to 675° C. The steam catalytic cracking reactor 180 may be operable to contact the hydrocarbon feed 110 with steam in the presence of the nano-zeolite cracking catalyst 187, which may cause steam catalytic cracking of at least a portion of the hydrocarbons in the hydrocarbon feed to produce a steam catalytic cracking effluent 210 comprising light olefins. The olefins may include ethylene, propylene, butenes, or combinations of these. In embodiments, operating the steam catalytic cracking system 100 in the ethylene-selective operating mode may produce a greater yield of ethylene compared to other operating modes or operating conditions. In embodiments, in the ethylene-selective operating mode, the steam catalytic cracking system 100 may produce a yield of ethylene that is greater than a yield of propylene. In embodiments, in the ethylene-selective operating mode, the steam catalytic cracking system 100 may achieve a yield ratio of ethylene to propylene of from 0.83 to 2, where the yield ratio comprises the yield of ethylene divided by the yield of propylene on a weight basis. In embodiments, in the ethylene-selective operating mode, the steam catalytic cracking system 100 may achieve a yield ratio of ethylene to propylene of from 1 to 2, on a weight basis. In embodiments, the steam catalytic cracking system 100 may produce a yield ratio of propylene to ethylene of from 0.5 to 1.2. The gaseous effluent 220 may be passed to one or more downstream processes for further separation into one or more product streams. The steam catalytic cracking system 100 may also produce the liquid hydrocarbon effluent 270 and the aqueous effluent 250.

Referring again to FIG. 2, in response to greater demand for propylene, the steam catalytic cracking reactor 180, which is configured in the first reactor configuration, may be operated instead in the propylene-selective operating mode. In the propylene-selective operating mode, the steam catalytic cracking system 100 may produce a greater proportion of propylene. The steam catalytic cracking system 100 may be transitioned to the propylene-selective mode in response to increasing market demand for propylene. In the propylene-selective operating mode, the steam catalytic cracking reactor 180 may be in the first reactor configuration in which the volume of the cracking catalyst charged to the steam catalytic cracking reactor 180 is such that the steam cracking catalyst zone 185 has a ratio of height $H_C$ to inside diameter ID of from 0.5 to 3.5. In the propylene-selective operating mode, the steam catalytic cracking reactor 180 may be operated at a lower temperature and a lower flow rate of the hydrocarbon feed 110 to the steam catalytic cracking reactor 180 compared to the ethylene-selective operating mode.

In the propylene-selective operating mode, the hydrocarbon feed 110 may be introduced to the steam catalytic cracking reactor 180. The hydrocarbon feed 110 may have any of the compositions previously discussed in the present disclosure. In embodiments, the hydrocarbon feed 110 may include crude oil and from 5 wt. % to 50 wt. % of one or more of straight run naphtha, light naphtha, middle range naphtha, heavy range naphtha, whole range bunker fuel cut up to 620° C., light condensate gas shale, vacuum gas oil (VGO), or combinations of these. The hydrocarbon feed 110 may be heated to a temperature of from 20° C. to 85° C. and then introduced to a feed pump 130. In the propylene-selective operating mode, the flow rate of the hydrocarbon feed 110 is injected into the steam catalytic cracking reactor 180 at a liquid hourly space velocity of from 0.05 $h^{-1}$ to 5 $h^{-1}$, such as at a liquid hourly space velocity of from 0.05 $h^{-1}$ to 0.8 $h^{-1}$, from 0.05 $h^{-1}$ to 0.5 $h^{-1}$, from 0.3 $h^{-1}$ to 0.8 $h^{-1}$, or from 0.3 $h^{-1}$ to 0.5 $h^{-1}$. The hydrocarbon feed 110 may be further pre-heated in feed inlet line 150 to a temperature between 70° C. to 150° C. before injecting the hydrocarbon feed 110 into the steam catalytic cracking reactor 180.

Water 120 may be injected into the steam catalytic cracking reactor 180 through water line 160 via the water pump 140. The water 120 may be pre-heated at a temperature of from 10° C. to 55° C. The water line 160 may be pre-heated to a temperature of from 70° C. to 150° C. The water may be converted to steam in water line 160 or upon contact with the hydrocarbon feed 110 in the steam catalytic cracking reactor 180. The flow rate of the water pump 140 may be adjusted so that the water 120 is injected into the steam catalytic cracking reactor 180 at a liquid hourly space velocity of 0.5 $h^{-1}$ to 50 $h^{-1}$, such as from 1 $h^{-1}$ to 10 $h^{-1}$.

The hydrocarbon feed 110 and the water 120 are injected into the steam catalytic cracking reactor 180. The water 120 and hydrocarbon feed 110 may flow into the steam catalytic cracking reactor in a ratio of water to hydrocarbon of from 50 to 1, such as from 5 to 1. The hydrocarbon feed and the water may mix before being superheated in the inert carrier pre-heating zone 189 to a temperature of from 90° C. to 250° C. to further induce mixing. The inert carrier pre-heating zone 189 may be loaded with porous packing material 183, such as silica carbide. The porous packing material 183 may be loaded relative to the loaded cracking catalyst (nano-zeolite cracking catalyst 187) in a ratio of porous packing material to catalyst of from 0.1 to 4, such as from 1 to 2.

The superheated hydrocarbon feed and steam mixture then flows into the steam cracking catalyst zone 185. In the propylene-selective operating mode, the steam cracking catalyst zone 185 may be operated at a temperature of from 540° C. to 620° C., such as from 570° C. to 615° C. The steam catalytic cracking reactor 180 may be operable to contact the hydrocarbon feed 110 with steam in the presence of the nano-zeolite cracking catalyst 187, which may cause steam catalytic cracking of at least a portion of the hydrocarbons in the hydrocarbon feed 110 to produce a steam catalytic cracking effluent 210 comprising light olefins. The olefins may include ethylene, propylene, butenes, or combinations of these. In embodiments, the steam catalytic cracking system 100 may achieve a yield ratio of propylene to ethylene of from 1.2 to 3.5, such as from 1.5 to 3.5 or from 2 to 3.5, where the yield ratio comprises the yield of ethylene divided by the yield of propylene, on a per weight basis. In embodiments, the steam catalytic cracking system 100 may produce a yield ratio of ethylene to propylene of from 0.3 to 0.8. The gaseous effluent 220 may be passed to one or more downstream processes for further separation into one or more product streams. The steam catalytic cracking system 100 may also produce the liquid hydrocarbon effluent 270 and the aqueous effluent 250.

Figure 3:
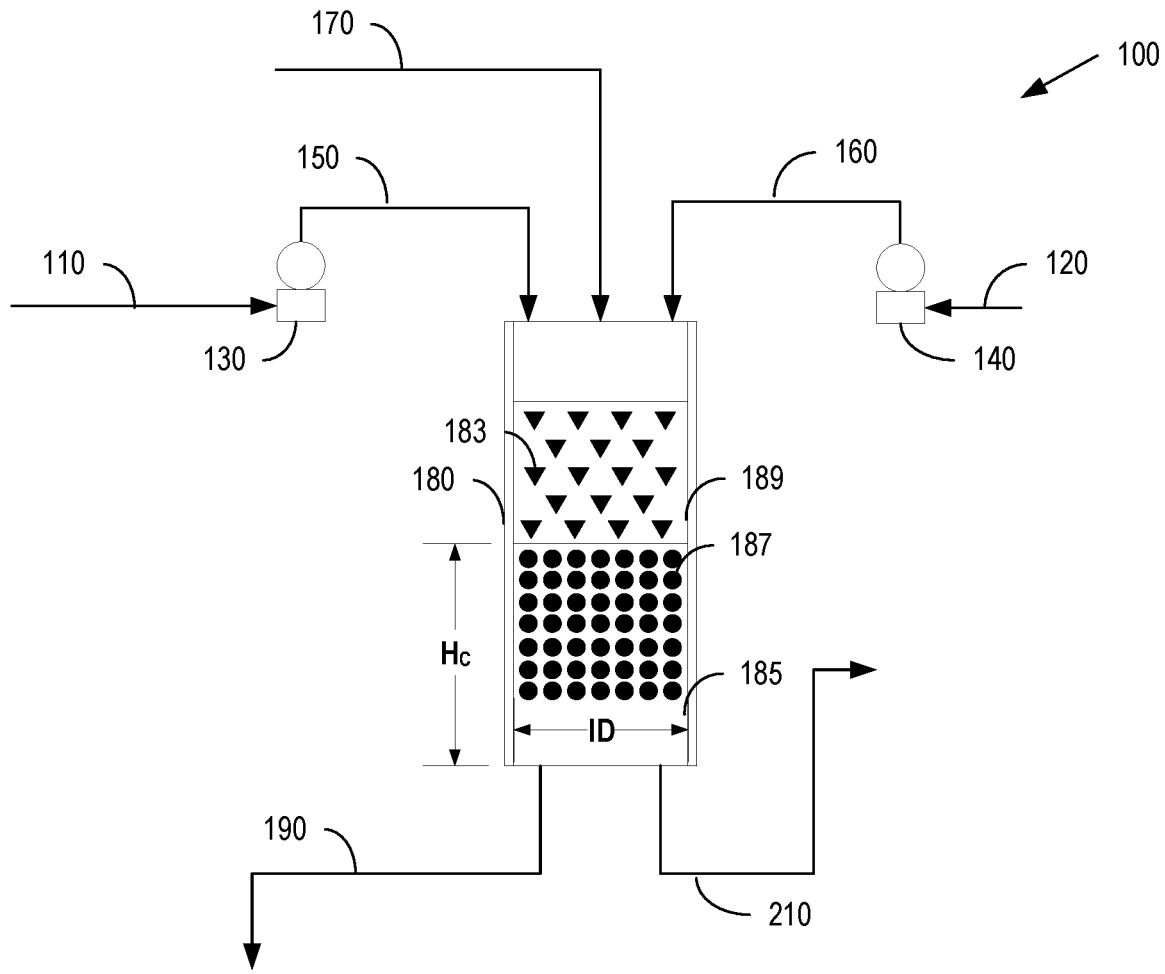
FIG. 3 schematically depicts a second configuration of the steam catalytic cracking reactor of the system of FIG. 1, according to one or more embodiments shown and described in this disclosure.

Referring now to FIG. 3, the steam catalytic cracking reactor 180 may be configured according to the second reactor configuration. In the second reactor configuration, the steam catalytic cracking reactor 180 may be operated in the third operating mode, which is a high-throughput propylene-selective mode. The steam catalytic cracking reactor 180 may be transitioned to the second reactor configuration when market demand for propylene indicates that additional capacity for producing propylene is needed above what can be produced through the propylene-selective mode in the first reactor configuration. In the second reactor configuration, the cracking catalyst 187 may be loaded into the steam cracking catalyst zone 185 of the steam catalytic cracking reactor 180 in an amount that results in the steam cracking catalyst zone 185 having a ratio of height $H_C$ to inside diameter ID of from 4.5 to 8, such as from 4.5 to 8, from 4.5 to 7.5, from 4.5 to 7, from 4.5 to 6.5, from 4.5 to 6, from 5 to 8, from 5 to 7.5, from 5 to 7, from 5 to 6.5, from 5 to 6, from 5.5 to 8, from 5.5 to 7.5, from 5.5 to 7, from 5.5 to 6.5, or about 6. The height $H_C$ is the distance from the top of the steam cracking catalyst zone 185 to the bottom of the steam cracking catalyst zone 185. The inside diameter ID is the inner diameter of the steam cracking catalyst zone 185. The cracking catalyst 187 may be any cracking catalyst described herein as being suitable for the steam catalytic cracking reactor 180. The volume of cracking catalyst 187 loaded into the steam cracking catalyst zone 185 may have a height of from 3 to 12 units, such as about 6 units. A unit may be defined as a centimeter, meter, inch, foot and/or yard. The cracking catalyst 187 may be loaded into the steam cracking catalyst zone 185 with diameter of from 0.5 to 4 units, such as about 1 unit. The cracking catalyst 187 may be loaded into the cracking reactor zone with a volume of from 0.59 to 150.8 cubic units, such as about 4.71 cubic units. Once the cracking catalyst 187 is loaded into the steam catalytic cracking reactor 180, the porous packing material 183 may be loaded on top of the cracking catalyst 187. In embodiments, the volume of porous packing material 183 may be sufficient to fill the remaining internal volume of the steam catalytic cracking reactor 180 up to the inlet feed distributors 151 and 161.

Referring again to FIG. 3, the steam catalytic cracking system 100 may be operable in the high-throughput propylene-selective mode. The steam catalytic cracking system 100 may be transitioned to the second reactor configuration and the high-throughput propylene-selective mode in response to further increasing market demand for propylene. In the high-throughput propylene-selective mode, the steam catalytic cracking reactor 180 may be in the second reactor configuration in which the volume of the cracking catalyst charged to the steam cracking cracking reactor 180 is such that the steam cracking catalyst zone 185 has a ratio of height $H_C$ to inside diameter ID of from 4.5 to 8. In the high-throughput propylene-selective mode, the steam catalytic cracking reactor 180 may be operated at the lower temperature range for increasing selectivity to propylene but at a greater flow rate of the hydrocarbon feed 110 to the steam catalytic cracking reactor 180 compared to the propylene-selective operating mode in the first reactor configuration.

The hydrocarbon feed 110 may be introduced to the steam catalytic cracking reactor 180. The hydrocarbon feed 110 may have any of the compositions previously discussed in the present disclosure. In embodiments, the hydrocarbon feed 110 may include crude oil and from 5 wt. % to 50 wt. % of one or more of straight run naphtha, light naphtha, middle range naphtha, heavy range naphtha, whole range bunker fuel cut up to 620° C., light condensate gas shale, vacuum gas oil (VGO), or combinations of these. The hydrocarbon feed 110 may be heated to a temperature of from 20° C. to 85° C. and then introduced to a feed pump 130. In the high-throughput propylene-selective mode, the hydrocarbon feed 110 may be injected into the steam catalytic cracking reactor 180 at a liquid hourly space velocity of from 0.05 $h^{-1}$ to 5 $h^{-1}$, such as at a liquid hourly space velocity of from 1 $h^{-1}$ to 5 $h^{-1}$, from 1 $h^{-1}$ to 4 $h^{-1}$, from 1 $h^{-1}$ to 3 $h^{-1}$, from 2 $h^{-1}$ to 5 $h^{-1}$, from 2 $h^{-1}$ to 4 $h^{-1}$, or even from 2 $h^{-1}$ to 3 $h^{-1}$. The hydrocarbon feed 110 may be further pre-heated in feed inlet line 150 to a temperature between 70° C. to 150° C. before injecting the hydrocarbon feed 110 into the steam catalytic cracking reactor 180.

Water 120 may be injected into the steam catalytic cracking reactor 180 through water line 160 via the water pump 140. The water 120 may be pre-heated at a temperature of from 10° C. to 55° C. The water line 160 may be pre-heated to a temperature of from 70° C. to 150° C. The water may be converted to steam in water line 160 or upon contact with the hydrocarbon feed 110 in the steam catalytic cracking reactor 180. The flow rate of the water pump 140 may be adjusted so that the water 120 is injected into the steam catalytic cracking reactor 180 at a liquid hourly space velocity of from 0.5 $h^{-1}$ to 50 $h^{-1}$, such as from 1 $h^{-1}$ to 10 $h^{-1}$.

The hydrocarbon feed 110 and the water 120 are injected into the steam catalytic cracking reactor 180. The water 120 and hydrocarbon feed 110 may flow into the steam catalytic cracking reactor in a ratio of water to hydrocarbon of from 50 to 1, such as from 5 to 1. The hydrocarbon feed and the water may mix before being superheated in the inert carrier pre-heating zone 189 to a temperature of from 90° C. to 250° C. to further induce mixing. The inert carrier pre-heating zone 189 may be loaded with porous packing material 183, such as silica carbide. The porous packing material 183 may be loaded relative to the loaded cracking catalyst in a ratio of porous packing material to catalyst of from 0.1 to 6, such as from 1 to 3.

The superheated hydrocarbon feed and steam mixture then flows into the steam cracking catalyst zone 185. In the high-throughput propylene-selective mode, the steam cracking catalyst zone 185 may operate at a temperature of from 540° C. to 620° C., such as from 570° C. to 615° C. The steam catalytic cracking reactor 180 may be operable to contact the hydrocarbon feed 110 with steam in the presence of the nano-zeolite cracking catalyst 187, which may cause steam catalytic cracking of at least a portion of the hydrocarbons in the hydrocarbon feed 110 to produce a steam catalytic cracking effluent 210 comprising light olefins. The olefins may include ethylene, propylene, butenes, or combinations of these. In embodiments, operating the steam catalytic cracking system 100 in the high-throughput propylene-selective mode may produce a greater yield of propylene compared to other operating conditions. In embodiments, in the high-throughput propylene operating mode, the steam catalytic cracking system 100 may produce a yield of propylene that is greater than a yield of ethylene. In embodiments, the steam catalytic cracking system 100 may achieve a yield ratio of propylene to ethylene of from 1.2 to 3.5, such as from 1.5 to 3.5 or even 2 to 3.5, where the yield comprises the yield of propylene divided by the yield of ethylene, on a weight basis. In embodiments, the steam catalytic cracking system 100 may produce a yield ratio of ethylene to propylene of from 0.3 to 0.8. Due to the greater flow rate of the hydrocarbon feed 110 to the steam catalytic cracking reactor 180, in the high-throughput propylene-selective mode, the production rate of propylene is greater. The gaseous effluent 220 may be passed to one or more downstream processes for further separation into one or more product streams. The steam catalytic cracking system 100 may also produce the liquid hydrocarbon effluent 270 and the aqueous effluent 250.

Referring again to FIG. 1, the steam catalytic cracking system 100 may further include a cracking effluent separation system 200 disposed downstream of the steam catalytic cracking reactor 180. When the steam catalytic cracking system 100 includes a plurality of steam catalytic cracking reactors 180, such as discussed in more detail with respect to FIG. 4, the steam catalytic cracking effluents 210 from each of the steam catalytic cracking reactors 180 may be passed to a single shared cracking effluent separation system 200. In embodiments, each steam catalytic cracking reactor 180 may have a dedicated cracking effluent separation system 200. The steam catalytic cracking effluent 210 may be passed from the steam catalytic cracking reactor 180 directly to the cracking effluent separation system 200. The cracking effluent separation system 200 may separate the steam catalytic cracking effluent 210 into one or more than one cracking product effluents, which may be liquid or gaseous product effluents.

Referring again to FIG. 1, the cracking effluent separation system 200 may include one or a plurality of separation units. In embodiments, the cracking effluent separation system 200 may include the gas-liquid separation unit 260 and an in-line centrifuge unit 240 downstream of the gas-liquid separation unit 260. The gas-liquid separation unit 260 may operate to separate the steam catalytic cracking effluent 210 into a gaseous effluent 220 and a liquid effluent 230. The gas-liquid separation unit 260 may operate to reduce the temperature of the steam catalytic cracking effluent 210 to condense constituents of the steam catalytic cracking effluent 210 having greater than or equal to 5 carbon atoms. The gas-liquid separation unit 260 may operate at a temperature of from 1° C. to 25° C. to ensure that normal pentane and constituents with boiling point temperatures greater than normal pentane are condensed into the liquid effluent 230. The liquid effluent 230 may include hydrocarbon blend such as naphtha, kerosene, gas oil, vacuum gas oil; unconverted feedstock; water; or combinations of these. The liquid effluent 230 may include at least 95%, at least 98%, at least 99%, or even at least 99.5% of the hydrocarbon constituents of the steam catalytic cracking effluent 210 having greater than or equal to 5 carbon atoms. The liquid effluent 230 may include at least 95%, at least 98%, at least 99%, or even at least 99.5% of the water from of the steam catalytic cracking effluent 210.

The gaseous effluent 220 may include olefins, such as ethylene, propylene, butenes, or combinations of these; light hydrocarbon gases, such as methane, ethane, propane, n-butane, i-butane, or combinations of these; other gases, such as but not limited to hydrogen; or combinations of these. The gaseous effluent 220 may include the $C_2$-$C_4$ olefin products, such as but not limited to, ethylene, propylene, butenes (1-butene, cis-2-butene, trans-2-butene, isobutene, or combinations of these), or combinations of these, produced in the steam catalytic cracking reactor 180. The gaseous effluent 220 may include at least 90%, at least 95%, at least 98%, at least 99%, or at least 99.5% of the $C_2$-$C_4$ olefins from the steam catalytic cracking effluent 210. The gaseous effluent 220 may be passed to a downstream gas separation system for further separation of the gaseous effluent 220 into various product streams, such as but not limited to one or more olefin product streams.

The liquid effluent 230, which includes the water and hydrocarbons having greater than 5 carbon atoms, may be passed to the in-line centrifuge unit 240. The in-line centrifuge unit 240 may operate to separate the liquid effluent 230 into a liquid hydrocarbon effluent 270 and an aqueous effluent 250. The in-line centrifuge unit 240 may be operated at a rotational speed of from 2500 rpm to 5000 rpm, from 2500 rpm to 4500 rpm, from 2500 rpm to 4000 rpm, from 3000 rpm to 5000 rpm, from 3000 rpm to 4500 rpm, or from 3000 rpm to 4000 rpm to separate the hydrocarbon phase from the aqueous phase.

The liquid hydrocarbon effluent 270 may include hydrocarbons from the steam catalytic cracking effluent 210 having greater than or equal to 5 carbon atoms. These hydrocarbons may include naphtha, kerosene, gas oil, vacuum gas oil (VGO), or combinations of these. The liquid hydrocarbon effluent 270 may include at 90%, at least 95%, at least 98%, at least 99%, or even at least 99.5% of the hydrocarbon constituents from the liquid effluent 230. The liquid hydrocarbon effluent 270 may be passed to a downstream treatment processes for further conversion or separation. At least a portion of the liquid hydrocarbon effluent 270 may be passed back to the steam catalytic cracking reactor 180 for further conversion to olefins. The aqueous effluent 250 may include water and water soluble constituents from the liquid effluent 230. The aqueous effluent 250 may include some dissolved hydrocarbons soluble in the aqueous phase of the liquid effluent 230. The aqueous effluent 250 may include at least 95%, at least 98%, at least 99%, or even at least 99.5% of the water from the liquid effluent 230. The aqueous effluent 250 may be passed to one or more downstream processes for further treatment. In embodiments, at least a portion of the aqueous effluent 250 may be passed back to the steam catalytic cracking reactor 180 as at least a portion of the water 120 introduced to the steam catalytic cracking reactor 180. Although described in the present disclosure as comprising a gas-liquid separation unit and a centrifuge, it is understood that any combination of separation processes suitable for separating the light olefin products from the steam catalytic cracking effluent are contemplated.

Referring again to FIG. 1, the processes for converting the hydrocarbon feed 110 to olefins may include contacting the hydrocarbon feed 110 with steam (from water 120) in the presence of the cracking catalyst in the steam catalytic cracking reactor 180 under reaction conditions sufficient to cause at least a portion of the hydrocarbons from the hydrocarbon feed 110 to undergo one or more cracking reactions to produce a steam catalytic cracking effluent 210 comprising light olefins. The process may further include separating the steam catalytic cracking effluent 210 through the cracking effluent separation system 200 into one or more of ethylene, propylene, butene, or combinations of these. The cracking effluent separation system 200 may be disposed downstream of the steam catalytic cracking reactor 180.

The process further includes determining whether to produce ethylene or propylene; when producing ethylene, then operating the process in the ethylene-selective mode, which produces more ethylene than propylene; or when producing propylene, then operating the process in the propylene-selective mode, which produces more propylene than ethylene.

Referring again to FIG. 2, the process for converting the hydrocarbon feed 110 to olefins in an ethylene-selective mode may include steam catalytic cracking the hydrocarbon feed in the presence of steam and a nano-zeolite cracking catalyst 187 disposed in a steam catalytic cracking reactor 180 of the steam catalytic cracking system 100 to produce a steam catalytic cracking effluent 210 comprising olefins. The cracking catalyst 187 may be loaded into the steam cracking catalyst zone 185 with a ratio of the height to diameter of the loaded cracking catalyst 187 of from 0.5 to 3.5, such as about 2. The process may be operated in an ethylene-selective mode at a reaction temperature of from 620° C. to 690° C., such as from 630° C. to 675° C. The hydrocarbon feed 110 may be injected into the steam catalytic cracking reactor 180 at a liquid hourly space velocity of from 0.05 h$^{-1}$ to 5 h$^{-1}$, such as from 0.03 h$^{-1}$ to 1.5 h$^{-1}$. The process may further include separating the steam catalytic cracking effluent 210 through the cracking effluent separation system 200 into one or more of ethylene, propylene, butene, or combinations of these. The cracking effluent separation system 200 may be disposed downstream of the steam catalytic cracking reactor 180. In the first reactor configuration run in the ethylene-selective mode, the process may achieve an ethylene to propylene yield of from 0.83 to 2.

Referring again to FIG. 2, the process for converting the hydrocarbon feed 110 to olefins operated in a propylene-selective mode may include steam catalytic cracking the hydrocarbon feed in the presence of steam and a nano-zeolite cracking catalyst 187 disposed in a steam catalytic cracking reactor 180 of the steam catalytic cracking system 100 to produce a steam catalytic cracking effluent 210 comprising olefins. The cracking catalyst 187 may be loaded into the steam cracking catalyst zone 185 with a ratio of the height to diameter of the loaded cracking catalyst 187 of from 0.5 to 3.5, such as about 2. The process may be operated in a propylene-selective mode at a reaction temperature of from 540° C. to 620° C., such as from 570° C. to 615° C. The hydrocarbon feed 110 may be injected into the steam catalytic cracking reactor 180 at a liquid hourly space velocity of from 0.05 h$^{-1}$ to 5 h$^{-1}$, such as from 0.03 h$^{-1}$ to 0.8 h$^{-1}$. The process may further include separating the steam catalytic cracking effluent 210 through the cracking effluent separation system 200 into one or more of ethylene, propylene, butene, or combinations of these. The cracking effluent separation system 200 may be disposed downstream of the steam catalytic cracking reactor 180. In the first reactor configuration run in the propylene-selective operating mode, the process may achieve a propylene to ethylene yield of from 1.2 to 3.5.

Referring again to FIG. 3, the process for converting the hydrocarbon feed 110 to olefins in a high-throughput propylene-selective mode may include steam catalytic cracking the hydrocarbon feed 110 in the presence of steam and a nano-zeolite cracking catalyst 187 disposed in a steam catalytic cracking reactor 180 of the steam catalytic cracking system 100 to produce a steam catalytic cracking effluent 210 comprising olefins. The cracking catalyst 187 may be loaded into the steam cracking catalyst zone 185 with a ratio of the height to diameter of the loaded cracking catalyst 187 of from 4.5 to 8, such as about 6. The process may be operated at a reaction temperature of from 540° C. to 620° C., such as from 570° C. to 615° C. The hydrocarbon feed 110 may be injected into the steam catalytic cracking reactor 180 at a liquid hourly space velocity of from 0.05 h$^{-1}$ to 5 h$^{-1}$, such as from 1 h$^{-1}$ to 5 h$^{-1}$. The process may further include separating the steam catalytic cracking effluent 210 through the cracking effluent separation system 200 into one or more of ethylene, propylene, butene, or combinations of these. The cracking effluent separation system 200 may be disposed downstream of the steam catalytic cracking reactor 180. In the high-throughput propylene-selective mode, the process may achieve a propylene to ethylene yield of from 1.2 to 3.5.

Referring again to FIG. 1, the process for converting the hydrocarbon feed 110 to olefins may include steam catalytic cracking the hydrocarbon feed in the presence of steam and a nano-zeolite cracking catalyst 187 disposed in a steam catalytic cracking reactor 180 of the steam catalytic cracking system 100 to produce a steam catalytic cracking effluent 210 comprising olefins. In embodiments, the process may further include transitioning the steam catalytic cracking reactor 180 from the propylene-selective mode to the ethylene-selective mode by maintaining or adjusting a load volume of the cracking catalyst in the reaction zone so that a ratio of height to diameter of the reaction zone 185 in the steam catalytic cracking reactor 180 is from 0.5 to 3.5. Transitioning the steam catalytic cracking reactor 180 from the propylene-selective mode to the ethylene-selective mode may also include adjusting the ratio of the inert carrier pre-heating loaded volume to the cracking catalyst loading volume into the range of from 0.1 to 6.

In embodiments, the process may further include operating the steam catalytic cracking reactor 180 in the ethylene-selective operating mode. In the ethylene-selective operating mode, the steam cracking catalyst zone 185 may be operated at a temperature of from 620° C. to 690° C., such as from 630° C. to 675° C. The steam catalytic cracking reactor 180 may be operable to contact the hydrocarbon feed 110 with steam in the presence of the nano-zeolite cracking catalyst 187, which may cause steam catalytic cracking of at least a portion of the hydrocarbons in the hydrocarbon feed 110 to produce a steam catalytic cracking effluent 210 comprising light olefins, including ethylene, propylene, butenes, or combinations of these. In embodiments, operating the steam catalytic cracking system 100 in the ethylene-selective operating mode may produce a greater yield of ethylene compared to other operating conditions. In embodiments, the steam catalytic cracking system 100 may achieve a yield ratio of ethylene to propylene of from 0.83 to 2, where the yield ratio comprises the yield of ethylene divided by the yield of propylene. In embodiments, the steam catalytic cracking system 100 may produce a yield ratio of propylene to ethylene of from 0.5 to 1.2.

In embodiments, the process may include transitioning the steam catalytic cracking reactor 180 from the ethylene-selective mode to the propylene-selective mode by maintaining or adjusting a load volume of the cracking catalyst 187 in the reaction zone 185 so that the ratio of height to diameter of the reaction zone 185 in the steam catalytic cracking reactor 180 is from 0.5 to 3.5. Transitioning the steam catalytic cracking reactor 180 from the ethylene-selective mode to the propylene-selective mode may also include adjusting the ratio of the inert carrier pre-heating 183 loaded volume to the cracking catalyst 187 loading volume in the range of from 0.1 to 4.

In embodiments, the process may further include operating the steam catalytic cracking reactor 180 in the propylene-selective operating mode. In the propylene-selective operating mode, the steam cracking catalyst zone 185 may be operates at a temperature of from 540° C. to 620° C., such as from 570° C. to 615° C. The steam catalytic cracking reactor 180 may be operable to contact the hydrocarbon feed 110 with steam in the presence of the nano-zeolite cracking catalyst 187, which may cause steam catalytic cracking of at least a portion of the hydrocarbons in the hydrocarbon feed 110 to produce a steam catalytic cracking effluent 210 comprising light olefins, including ethylene, propylene, butenes, or combinations of these. In embodiments, the steam catalytic cracking system 100 may achieve a yield ratio of propylene to ethylene of from 1.2 to 3.5, where the yield ratio comprises the yield of ethylene divided by the yield of propylene. In embodiments, the steam catalytic cracking system 100 may produce a yield ratio of ethylene to propylene of from 0.3 to 0.8.

In embodiments, the process may include transitioning the steam catalytic cracking reactor 180 to a high-throughput propylene-selective mode by maintaining or adjusting a load volume of the cracking catalyst 187 in the reaction zone 185 so that the ratio of the height to diameter of the reaction zone 185 in the steam catalytic cracking reactor 180 is from 4.5 to 8. Transitioning the steam catalytic cracking reactor 180 to the high-throughput propylene-selective mode may also include adjusting the ratio of the inert carrier pre-heating 183 loaded volume to the cracking catalyst 187 loading volume into a range of from 0.1 to 6.

In embodiments, the process may further include operating the steam catalytic cracking reactor 180 in the high-throughput propylene-selective operating mode. In the high-throughput propylene-selective mode, the steam cracking catalyst zone 185 may operate at a temperature of from 540° C. to 620° C., such as from 570° C. to 615° C. The steam catalytic cracking reactor 180 may be operable to contact the hydrocarbon feed 110 with steam in the presence of the nano-zeolite cracking catalyst 187, which may cause steam catalytic cracking of at least a portion of the hydrocarbons in the hydrocarbon feed 110 to produce a steam catalytic cracking effluent 210 comprising light olefins. The olefins may include ethylene, propylene, butenes, or combinations of these. In embodiments, operating the steam catalytic cracking system 100 in the high-throughput propylene-selective mode may produce a greater yield of propylene compared to other operating conditions. In embodiments, in the high-throughput propylene operating mode, the steam catalytic cracking system 100 may produce a yield of propylene that is greater than a yield of ethylene. In embodiments, the steam catalytic cracking system 100 may achieve a yield ratio of propylene to ethylene yield of from 1.2 to 3.5, where the yield comprises the yield of propylene divided by the yield of ethylene. In embodiments, the steam catalytic cracking system 100 may produce a yield ratio of ethylene to propylene of from 0.3 to 0.8.

Figure 4:
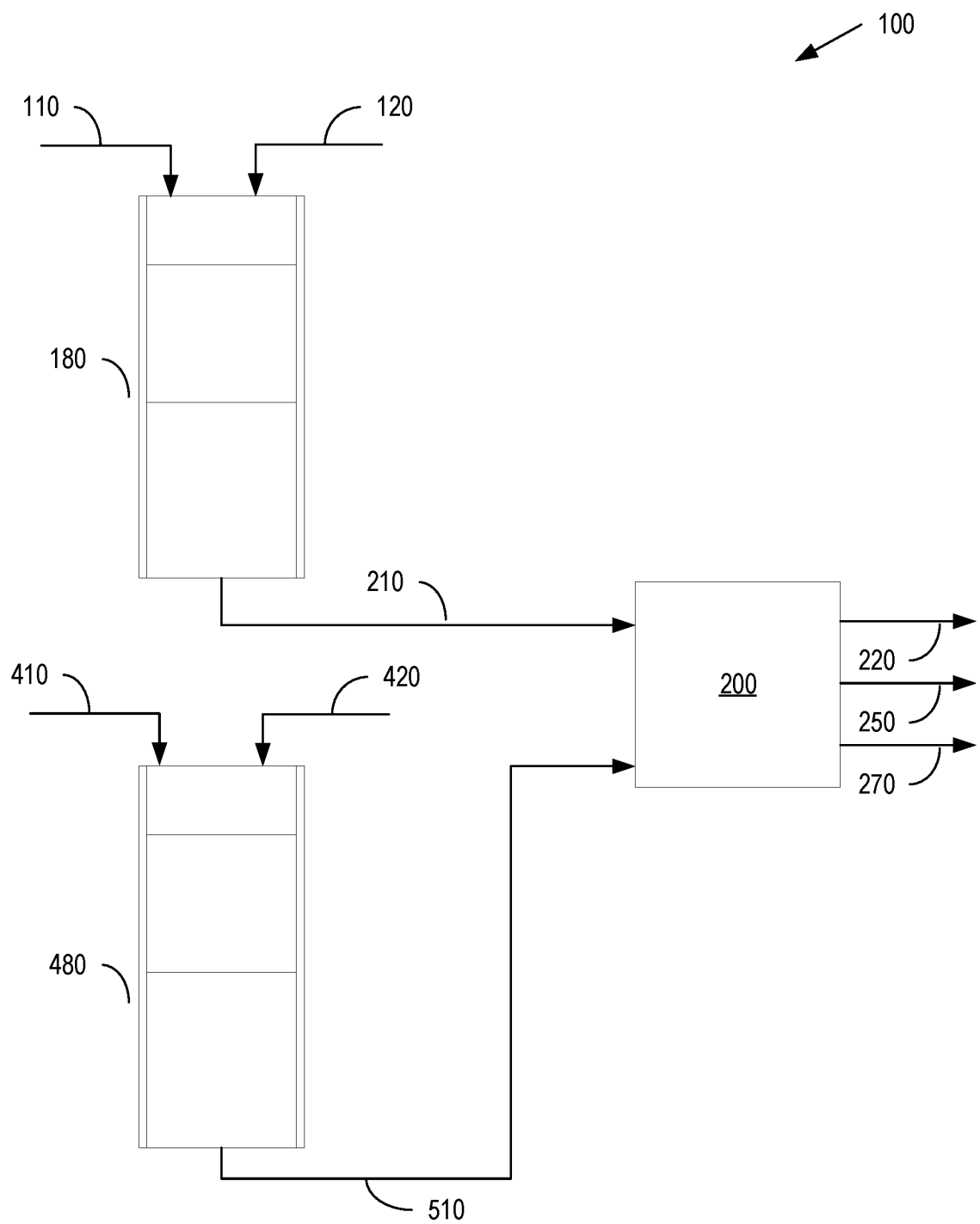
FIG. 4 schematically depicts a generalized flow diagram of another embodiment of a system for converting heavy hydrocarbon feeds to light olefins, according to one or more embodiments shown and described in this disclosure.

Referring now to FIG. 4, the steam catalytic cracking system 100 may include a first steam catalytic cracking reactor 180 and a second steam catalytic cracking reactor 480. The second steam catalytic cracking reactor 480 may be operated in parallel with the first steam catalytic cracking reactor 180. In embodiments, each of the first steam catalytic cracking reactor 180 and the second steam catalytic cracking reactor 480 may include a plurality of steam cracking reactors operated in parallel so that continuous operation of the steam catalytic cracking system 100 can be maintained, while also regenerating the nano-zeolite cracking catalyst 187. Each of the steam catalytic cracking reactors operated in parallel may be configured independently in either the first reactor configuration or the second reactor configuration and operated in either the ethylene-selective, propylene-selective, or high-throughput propylene-selective modes, so that continuous operation of the steam catalytic cracking system 100 can be maintained, while also converting the hydrocarbon feed to increased ethylene yield or increased propylene yield, such as due to varying product demand. In embodiments, the first steam catalytic cracking reactor 180 may be configured in a first configuration and operated in an ethylene-selective mode or a propylene-selective mode, and the second steam catalytic cracking reactor 480 may be configured in a second configuration and operated in a high-throughput propylene-selective mode. In embodiments, the first steam catalytic cracking reactor 180 may be configured in a first configuration and operated in an ethylene-selective mode or a propylene-selective mode, and the second steam catalytic cracking reactor 480 may also be configured in a first configuration and operated in an ethylene-selective mode or a propylene-selective mode. In embodiments, the first steam catalytic cracking reactor 180 may be configured in a second configuration and operated in a high-throughput propylene-selective mode, and the second steam catalytic cracking reactor 480 may also be configured in a second configuration and operated in a high-throughput propylene-selective mode. In embodiments, the first steam catalytic cracking reactor 180 may be configured in a second configuration and operated in a high-throughput propylene-selective mode, the second steam catalytic cracking reactor 480 may also be configured in a first configuration and operated in an ethylene-selective mode or a propylene-selective mode. Referring again to FIG. 4, in operation of steam catalytic cracking system 100 for converting hydrocarbon feed 110 to olefins, the hydrocarbon feed 110 may be passed to both the first steam catalytic cracking reactor 180 and the second steam catalytic cracking reactor 480. The first steam catalytic cracking reactor 180 may contact the hydrocarbon feed 110 to produce olefins, such as ethylene, propylene, butenes, or combinations of these. The second steam catalytic cracking reactor 480 may contact the hydrocarbon feed 110 to produce olefins, such as ethylene, propylene, butenes, or combinations of these.

Referring again to FIG. 4, the first steam catalytic cracking reactor 180 and the second steam catalytic cracking reactor 480 may share a common cracking effluent separation system 200. A first steam catalytic cracking effluent 210 may be passed from the first steam catalytic cracking reactor 180 to the cracking effluent separation system 200. A second steam catalytic cracking effluent 510 may be passed from the second steam catalytic cracking reactor 480 to the cracking effluent separation system 200. As previously discussed, the cracking effluent separation system 200 may be operable to separate the effluents from the steam catalytic cracking reactors 180, 480 into the gaseous effluent 220 comprising the olefin products, the liquid hydrocarbon effluent 270, and the aqueous effluent 250. Although depicted in FIG. 4 as having a single common shared cracking effluent separation system 200, it is understood that each of the steam catalytic cracking reactors could have a steam catalytic cracking effluent separation system.

EXAMPLES

The various embodiments of methods and systems for the processing of a hydrocarbon feed to produce olefins will be further clarified by the following examples. The examples are illustrative in nature, and should not be understood to limit the subject matter of the present disclosure.

Example 1: Configuration 1—Setting 1
Ethylene-Selective Mode

Example 1 was conducted at a pilot plant having the first reactor configuration and characteristics of the steam catalytic cracking reactor 180 illustrated in FIG. 2. In Example 1, the steam catalytic cracking reactor of the present disclosure was operated in the ethylene-selective mode to obtain light olefins from a hydrocarbon feed.

The hydrocarbon feed comprised 20 wt. % naphtha preheated to from 93° C. to 205° C. and 80 wt. % vacuum gas oil heated to from 370° C. to 590° C. was passed to a fixed bed steam catalytic cracking reactor. The hydrocarbon feed was preheated and the preheated feed at 70° C. was introduced to the reactor at space velocity of 0.5 hourly ($h^{-1}$) and steam was injected at space velocity of 1 hourly ($h^{-1}$). The steam to oil volume ratio was 2 to 1. The steam catalytic cracking was carried out in the steam catalytic cracking reactor loaded with nano ZSM-5 zeolite bounded with 40 wt. % alumina binder. The catalyst was loaded into the steam catalytic cracking reactor forming a cylindrical catalyst bed arranged with a height of 4 units and diameter of 2 units. The catalyst loading height to diameter ratio was 2 to 1, for a ratio of height $H_C$ to inside diameter ID of 2. The inert carrier pre-heating zone of the steam catalytic cracking reactor was loaded with silica carbide. The inert carrier pre-heating loaded volume to catalyst loaded volume ratio was 2 to 1. The catalyst bed zone and the inert carrier pre-heating zone were operated at 650° C.

As shown in Table 3, the steam catalytic cracking process of Example 1 operated in the ethylene-selective mode achieved high conversion. High yield of olefins 51 wt. % with a yield ratio of ethylene/propylene of 1.1 was obtained.

TABLE 3

Composition of steam catalytic cracking effluent from Example 1

| Constituent | Example 1 Yield (wt. %) |
|---|---|
| Naphtha | 14.2 |
| Gas oil | 8.2 |
| VGO | 8.7 |
| Olefins | 51 |
| Ethylene | 20.8 |
| Propylene | 18.0 |
| Butenes | 12.2 |
| P/E | 0.9 |
| LPG | 1.8 |
| Dry gas | 13.6 |

Example 2: Configuration 1—Setting 2 Propylene-Selective Mode

Example 2 was conducted at a pilot plant having the first reactor configuration and characteristics of steam catalytic cracking reactor 180 illustrated in FIG. 2. In Example 2, the steam catalytic cracking reactor of the present disclosure was operated in the propylene-selective mode to obtain light olefins from a hydrocarbon feed.

The hydrocarbon feed comprised 20 wt. % naphtha preheated to from 93° C. to 205° C. and 80 wt. % vacuum gas oil heated to from 370° C. to 590° C. was passed to a fixed bed steam catalytic cracking reactor. The hydrocarbon feed was preheated and the preheated feed at 70° C. was introduced to the reactor at space velocity of 0.5 hourly ($h^{-1}$) and steam was injected at space velocity of 1 hourly ($h^{-1}$). The steam to oil volume ratio was 2 to 1. The steam catalytic cracking was carried out in the steam catalytic cracking reactor loaded with nano ZSM-5 zeolite bounded with 40 wt. % alumina binder. The catalyst was loaded into the steam catalytic cracking reactor forming a cylindrical catalyst bed arranged with a height of 4 units and diameter of 2 units. The catalyst loading height to diameter ratio was 2 to 1, for a ratio of height $H_C$ to inside diameter ID of 2. The inert carrier pre-heating zone of the steam catalytic cracking reactor was loaded with silica carbide. The inert carrier pre-heating loaded volume to catalyst loaded volume ratio was 2 to 1. The catalyst bed zone and the inert carrier pre-heating zone were operated at 575° C.

As shown in Table 4, the steam catalytic cracking process operated in the propylene-selective mode achieved high conversion. High yield of olefins 49 wt. % with a yield ratio of propylene/ethylene of 1.87 was obtained.

TABLE 4

Composition of steam catalytic cracking effluent from Example 2

| Consistent | Example 2 Yield (wt. %) |
|---|---|
| Naphtha | 10.4 |
| Gas oil | 13.2 |
| VGO | 16.1 |
| Olefins | 49 |
| Ethylene | 10.8 |
| Propylene | 20.3 |
| Butenes | 17.9 |
| P/E | 1.9 |
| LPG | 2.9 |
| Dry gas | 7.1 |

Example 3: Configuration 2—Setting 3 High-Throughput Propylene-Selective Mode

Example 3 was conducted at a pilot plant having the second reactor configuration and characteristics of steam catalytic cracking reactor 180 illustrated in FIG. 3. In Example 3, the steam catalytic cracking reactor of the present disclosure was operated in the high-throughput propylene-selective mode to obtain light olefins from a hydrocarbon feed.

The hydrocarbon feed comprised 20 wt. % naphtha preheated to from 93° C. to 205° C. and 80 wt. % vacuum gas oil heated to from 370° C. to 590° C. was passed to a fixed bed steam catalytic cracking reactor. The hydrocarbon feed was preheated and the preheated feed at 70° C. was introduced to the reactor at space velocity of 1 hourly ($h^{-1}$) and steam was injected at space velocity of 2 hourly ($h^{-1}$). The steam to oil volume ratio was 2 to 1. The steam catalytic cracking was carried out in the steam catalytic cracking reactor loaded with nano ZSM-5 zeolite bounded with 40 wt. % alumina binder. The catalyst was loaded into the steam catalytic cracking reactor forming a cylindrical catalyst bed arranged with a height of 6 units and diameter of 1 units. The catalyst loading height to diameter ratio was 6 to 1, for a ratio of height $H_C$ to inside diameter ID of 6. The inert carrier pre-heating zone of the steam catalytic cracking reactor was loaded with silica carbide. The inert carrier pre-heating loaded volume to catalyst loaded volume ratio was 2 to 1. The catalyst bed zone and the inert carrier pre-heating zone was operated at 600° C.

As shown in Table 5, the steam catalytic cracking process operated in the high-throughput propylene-selective mode in Example 3 achieved high conversion. High yield of olefins 57.5 wt. % with a yield ration of propylene/ethylene of 2.8 was obtained.

TABLE 5

Composition of steam catalytic cracking effluent from Example 3

| Consistent | Example 3 Yield (wt. %) |
|---|---|
| Naphtha | 6.1 |
| Gas oil | 9 |
| VGO | 16.6 |

TABLE 5-continued

Composition of steam catalytic cracking effluent from Example 3

| Consistent | Example 3 Yield (wt. %) |
|---|---|
| Olefins | 57.5 |
| Ethylene | 11 |
| Propylene | 30.3 |
| Butenes | 16.3 |
| P/E | 2.7 |
| LPG | 3 |
| Dry gas | 4.1 |

One or more aspects of the present disclosure are described herein. A first aspect of the present disclosure may include a process for upgrading a hydrocarbon feed to produce light olefins, the process comprising contacting the hydrocarbon feed with steam in the presence of a cracking catalyst in a steam catalytic cracking reactor at reaction conditions sufficient to cause at least a portion of the hydrocarbons in the hydrocarbon feed to undergo one or more cracking reactions to produce a steam catalytic cracking effluent comprising ethylene, propylene, or both, wherein the process is capable of being transitioned between an ethylene selective mode and a propylene selective mode. The process may further comprise determining whether to produce ethylene or propylene and when producing ethylene, then operating the process in ethylene selective mode comprises producing more ethylene than propylene; or when producing propylene, then operating the process in propylene selective mode comprises producing more propylene than ethylene.

A second aspect of the present disclosure may include the first aspect, where the hydrocarbon feed may comprise at least one of: a crude oil, a light naphtha feed, a light condensate gas shale feed, a middle range naphtha feed, a heavy range naphtha feed, a kerosene feed, a whole range vacuum gas oil feed, a bunker fuel feed, or combinations of these materials.

A third aspect of the present disclosure may include any one of the first through second aspects, where the cracking catalyst comprises a zeolite and a binder, where the zeolite comprises a nano ZSM-5 zeolite.

A fourth aspect of the present disclosure may include any one of the first through third aspects, wherein the cracking catalyst comprises: from 1 wt. %-99 wt. % nano ZSM-5 zeolite based on the total weight of zeolite in the cracking catalyst; and from 1 wt. %-99 wt. % of a zeolite selected from the group consisting of a nano BEA zeolite, a nano Y-type zeolite, a nano mordenite zeolite, or combinations of these.

A fifth aspect of the present disclosure may include any one of the third through fourth aspects, wherein the nano-ZSM-5 zeolite has an average crystal size of from 0.1 nm to 900 nm.

A sixth aspect of the present disclosure may include any one of the third through fifth aspects, wherein the nano ZSM-5 zeolite has a molar ratio of silica to alumina of from 1 to 1000.

A seventh aspect of the present disclosure may include any one of the first through sixth aspects, wherein the cracking catalyst comprises from 1 wt. % to 90 wt. % nano ZSM-5 zeolite and from 10 wt. % to 90 wt. % binder based on the total weight of the cracking catalyst.

An eighth aspect of the present disclosure may include any one of the first through seventh aspects, further comprising introducing the hydrocarbon feed to the steam catalytic cracking reactor; and introducing water to the steam catalytic cracking reactor at a liquid hourly space velocity of from 0.5 per hour to 50 per hour.

A ninth aspect of the present disclosure may include any one of the first through eighth aspects, further comprising determining to operate the process in the ethylene selective mode; transitioning the process from the propylene selective mode to the ethylene selective mode; and operating the process in the ethylene selective mode.

A tenth aspect of the present disclosure may include the ninth aspect, wherein the steam catalytic cracking reactor comprises a preheating zone and a reaction zone downstream of the preheating zone, wherein the preheating zone comprises an inert carrier and the reaction zone comprises the cracking catalyst, and transitioning the process from the propylene selective mode to the ethylene selective mode comprising maintaining or adjusting a loading volume of the cracking catalyst in the reaction zone so that a ratio of height to diameter of the reaction zone in the steam catalytic cracking reactor is from 0.5 to 3.5; and adjusting the inert carrier pre-heating loaded volume to the cracking catalyst loading volume ranges from 0.1 to 6.

An eleventh aspect of the present disclosure may include any one of the first through tenth aspects, wherein operating the process in the ethylene selective mode comprises contacting the hydrocarbon with the steam in the presence of the cracking catalyst at a reaction temperature of from 620 degrees Celsius (° C.) to 690° C. and a liquid hourly space velocity of the hydrocarbon feed of from 0.05 per hour to 5 per hour.

A twelfth aspect of the present disclosure may include any one of the first through eleventh aspects, further comprising recovering a cracking effluent from the steam catalytic cracking reactor, where the cracking effluent has a weight ratio of ethylene to propylene of from 0.8 to 2.

A thirteenth aspect of the present disclosure may include any one of the first through eight aspects, further comprising determining to operate the process in the propylene selective mode; transitioning the process from the ethylene selective mode to the propylene selective mode; and operating the process in the propylene selective mode.

A fourteenth aspect of the present disclosure may include the thirteenth aspect, wherein the steam catalytic cracking reactor comprises a preheating zone and a reaction zone downstream of the preheating zone, wherein the preheating zone comprises an inert carrier and the reaction zone comprises the cracking catalyst; and transitioning the process from the ethylene selective mode to the propylene selective mode comprises maintaining or adjusting a loading volume of the cracking catalyst in the reaction zone so that height to diameter ratio of the reaction zone in the steam catalytic cracking reactor is from 0.5 to 3.5, and adjusting the inert carrier pre-heating loaded volume to the cracking catalyst loading volume ranges from 0.1 to 4.

A fifteenth aspect of the present disclosure may include any one of the first through fourteenth aspects, wherein operating the process in the propylene selective mode comprises contacting the hydrocarbon with the steam in the presence of the cracking catalyst at a reaction temperature of from 540 degrees Celsius (° C.) to 620° C. and a liquid hourly space velocity of the hydrocarbon feed pump ranges from 0.05 per hour to 1.5 per hour.

A sixteenth aspect of the present disclosure may include the fifteenth aspect, further comprising recovering a cracking effluent from the steam catalytic cracking reactor, where the cracking effluent has a weight ratio of ethylene to propylene of from 0.3 to 0.8.

A seventeenth aspect of the present disclosure may include any of the first through eighth aspects, comprising determining to operate in a high-throughput propylene selective mode; transitioning the steam catalytic cracking reactor to the high-throughput propylene selective mode; and operating the process in the high-throughput propylene selective mode.

An eighteenth aspect of the present disclosure may include the seventeenth aspect, wherein the steam catalytic cracking reactor comprises a preheating zone and a reaction zone downstream of the preheating zone, wherein the preheating zone comprises an inert carrier and the reaction zone comprises the cracking catalyst; and transitioning the steam catalytic cracking reactor to the high-throughput propylene selective mode comprises adjusting a loading volume of the cracking catalyst in the reaction zone so that a height to diameter ratio of the reaction zone in the steam catalytic cracking reactor is from 4.5 to 8, and adjusting the inert carrier pre-heating loaded volume to the cracking catalyst loading volume ranges from 0.1 to 6.

A nineteenth aspect of the present disclosure may include any one of first through eighteenth aspects, wherein operating the process in the high-throughput propylene selective mode comprises contacting the hydrocarbon with the steam in the presence of the cracking catalyst at a reaction temperature of from 540 degrees Celsius (° C.) to 620° C. and a liquid hourly space velocity of the hydrocarbon feed pump ranges from 0.5 per hour to 5 per hour.

A twentieth aspect of the present disclosure may include any one of the first through nineteenth aspects, further comprising recovering a cracking effluent from the steam catalytic cracking reactor, where the cracking effluent has a weight ratio of ethylene to propylene of from 0.3 to 0.8.

A twenty-first aspect of the present disclosure may include any one of the first through twentieth aspects, further comprising recovering a cracking effluent from the steam catalytic cracking reactor, where the cracking effluent has a weight ratio of propylene to ethylene of from 1.2 to 3.5.

A twenty-second aspect of the present disclosure may include any one of the first through twenty-first aspect, further comprising regenerating the cracking catalyst.

A twenty-third aspect of the present disclosure may include the twenty-second aspect, where regenerating the cracking catalyst comprises: evacuating hydrocarbons and steam from the steam catalytic cracking reactor; passing an oxygen-containing gas to the steam catalytic cracking reactor at a gas hourly space velocity (GHSV) of from 10 per hour to 100 per hour; contacting the cracking catalyst with the oxygen-containing gas at a regeneration temperature of from 600° C. to 750° C. for a regeneration period of from 2 hours to 6 hours, where the contacting causes combustion of coke deposits on the cracking catalyst; venting the oxygen-containing gas from the steam catalytic cracking reactor; analyzing the oxygen-containing gas vented from the steam catalytic cracking reactor to determine a concentration of carbon dioxide in the oxygen-containing gas vented from the steam catalytic cracking reactor; determining when regeneration is completed based on the concentration of carbon dioxide in the oxygen-containing gas vented from the steam catalytic cracking reactor; and after determining when the regeneration is completed, ceasing the flow of oxygen-containing gas to the steam catalytic cracking reactor.

A twenty-fourth aspect of the present disclosure may include the twenty-third aspect further comprises restarting flow of the hydrocarbon feed.

A twenty-fifth aspect of the present disclosure may include any one of the twenty-second through twenty-third aspects, wherein determining when the regeneration is completed comprises determining when the concentration of the carbon dioxide in the oxygen-containing gas vented from the steam catalytic cracking reactor is in a range of from 0.05 wt. % to 0.2 wt. % based on the unit weight of the oxygen-containing gas vented from the steam catalytic cracking reactor.

A twenty-sixth aspect of the present disclosure may include a process for upgrading a hydrocarbon feed, the process comprising: configuring a steam catalytic cracking reactor in either an ethylene selective mode or a propylene selective mode, where configuring the steam catalytic cracking reactor comprises: selecting a configuration for the steam catalytic cracking reactor; selecting one or more settings for the steam catalytic cracking reactor; loading a cracking catalyst based on the one or more steam catalytic cracking reactor settings; loading an inert carrier pre-heating into the steam catalytic cracking reactor; adjusting a temperature for the steam catalytic cracking reactor based on the one or more steam catalytic cracking reactor settings; and adjusting a liquid hourly volumetric space velocity for one or more feed pumps in the steam catalytic cracking reactor; and contacting the hydrocarbon feed with steam in the presence of the cracking catalyst in the steam catalytic cracking reactor at reaction conditions sufficient to cause at least a portion of the hydrocarbons in the hydrocarbon feed to undergo one or more cracking reactions to produce a steam catalytic cracking effluent comprising ethylene, propylene, or both.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for upgrading a hydrocarbon feed to produce light olefins, the process comprising:
   contacting the hydrocarbon feed with steam in the presence of a cracking catalyst in a steam catalytic cracking reactor at reaction conditions sufficient to cause at least a portion of the hydrocarbons in the hydrocarbon feed to undergo one or more cracking reactions to produce a steam catalytic cracking effluent comprising ethylene, propylene, or both, wherein the process is capable of being transitioned between an ethylene-selective mode and a propylene-selective mode;

determining whether to produce ethylene or propylene;

when producing ethylene, then operating the process in ethylene-selective mode comprises producing more ethylene than propylene; or when producing propylene, then operating the process in propylene-selective mode comprises producing more propylene than ethylene.

2. The process of claim 1, wherein the hydrocarbon feed comprises at least one of:
a crude oil,
a light naphtha feed,
a light condensate gas shale feed,
a middle range naphtha feed,
a heavy range naphtha feed,
a kerosene feed,
a whole range vacuum gas oil feed,
a bunker fuel feed, or combinations of these materials.

3. The process of claim 1, where the cracking catalyst comprises a zeolite and a binder, wherein:
the cracking catalyst comprises from 1 wt. % to 90 wt. % zeolite and from 10 wt. % to 90 wt. % binder based on the total weight of the cracking catalyst; and
the zeolite comprises:
from 1 wt. %-99 wt. % nano ZSM-5 zeolite based on the total weight of zeolite in the cracking catalyst, wherein the nano-ZSM-5 zeolite has an average crystal size of from 0.1 nm to 900 nm and a molar ratio of silica to alumina of from 1 to 1000; and
from 1%-99% of a zeolite selected from the group consisting of a nano BEA zeolite, a nano Y-type zeolite, a nano mordenite zeolite, or combinations of these.

4. The process of claim 1, comprising:
introducing the hydrocarbon feed to the steam catalytic cracking reactor; and
introducing water to the steam catalytic cracking reactor at a liquid hourly space velocity of from 0.5 per hour to 50 per hour.

5. The process of claim 1, comprising:
determining to operate the process in the ethylene-selective mode;
transitioning the process from the propylene-selective mode to the ethylene-selective mode; and
operating the process in the ethylene-selective mode.

6. The process of claim 5, wherein:
the steam catalytic cracking reactor comprises a preheating zone and a reaction zone downstream of the preheating zone, wherein the preheating zone comprises an inert carrier and the reaction zone comprises the cracking catalyst; and
transitioning the process from the propylene-selective mode to the ethylene-selective mode comprises:
maintaining or adjusting a loading volume of the cracking catalyst in the reaction zone so that a ratio of height to diameter of the reaction zone in the steam catalytic cracking reactor is from 0.5 to 3.5; and adjusting the inert carrier pre-heating loaded volume to the cracking catalyst loading volume ranges from 0.1 to 6.

7. The process of claim 5, wherein operating the process in the ethylene-selective mode comprises contacting the hydrocarbon with the steam in the presence of the cracking catalyst at a reaction temperature of from 620 degrees Celsius (° C.) to 690° C. and a liquid hourly space velocity of the hydrocarbon feed of from 0.05 per hour to 5 per hour.

8. The process of claim 5, further comprising recovering a cracking effluent from the steam catalytic cracking reactor, where the cracking effluent has a weight ratio of ethylene to propylene of from 0.8 to 2.

9. The process of claim 1, comprising:
determining to operate the process in the propylene-selective mode;
transitioning the process from the ethylene-selective mode to the propylene-selective mode; and
operating the process in the propylene-selective mode.

10. The process of claim 9, wherein:
the steam catalytic cracking reactor comprises a preheating zone and a reaction zone downstream of the preheating zone, wherein the preheating zone comprises an inert carrier and the reaction zone comprises the cracking catalyst; and
transitioning the process from the ethylene-selective mode to the propylene-selective mode comprises maintaining or adjusting a loading volume of the cracking catalyst in the reaction zone so that height to diameter ratio of the reaction zone in the steam catalytic cracking reactor is from 0.5 to 3.5, and adjusting the inert carrier pre-heating loaded volume to the cracking catalyst loading volume ranges from 0.1 to 4.

11. The process of claim 9, wherein operating the process in the propylene-selective mode comprises contacting the hydrocarbon with the steam in the presence of the cracking catalyst at a reaction temperature of from 540 degrees Celsius (° C.) to 620° C. and a liquid hourly space velocity of the hydrocarbon feed pump ranges from 0.05 per hour to 1.5 per hour.

12. The process of claim 9, further comprising recovering a cracking effluent from the steam catalytic cracking reactor, where the cracking effluent has a weight ratio of ethylene to propylene of from 0.3 to 0.8.

13. The process of claim 1, comprising:
determining to operate in a high-throughput propylene-selective mode;
transitioning the steam catalytic cracking reactor to the high-throughput propylene-selective mode; and
operating the process in the high-throughput propylene-selective mode.

14. The process of claim 13, wherein:
the steam catalytic cracking reactor comprises a preheating zone and a reaction zone downstream of the preheating zone, wherein the preheating zone comprises an inert carrier and the reaction zone comprises the cracking catalyst; and
transitioning the steam catalytic cracking reactor to the high-throughput propylene-selective mode comprises adjusting a loading volume of the cracking catalyst in the reaction zone so that a height to diameter ratio of the reaction zone in the steam catalytic cracking reactor is from 4.5 to 8, and adjusting the inert carrier preheating loaded volume to the cracking catalyst loading volume ranges from 0.1 to 6.

15. The process of claim 13, wherein operating the process in the high-throughput propylene-selective mode comprises contacting the hydrocarbon with the steam in the presence of the cracking catalyst at a reaction temperature of from 540 degrees Celsius (° C.) to 620° C. and a liquid hourly space velocity of the hydrocarbon feed pump ranges from 0.5 per hour to 5 per hour.

16. The process of claim 13, further comprising recovering a cracking effluent from the steam catalytic cracking reactor, where the cracking effluent has a weight ratio of propylene to ethylene of from 1.2 to 3.5.

17. The process of claim 1, further comprising regenerating the cracking catalyst.

18. The process of claim 17, where regenerating the cracking catalyst comprises:
   evacuating hydrocarbons and steam from the steam catalytic cracking reactor;
   passing an oxygen-containing gas to the steam catalytic cracking reactor at a gas hourly space velocity (GHSV) of from 10 per hour to 100 per hour;
   contacting the cracking catalyst with the oxygen-containing gas at a regeneration temperature of from 600° C. to 750° C. for a regeneration period of from 2 hours to 6 hours, where the contacting causes combustion of coke deposits on the cracking catalyst;
   venting the oxygen-containing gas from the steam catalytic cracking reactor;
   analyzing the oxygen-containing gas vented from the steam catalytic cracking reactor to determine a concentration of carbon dioxide in the oxygen-containing gas vented from the steam catalytic cracking reactor;
   determining when regeneration is completed based on the concentration of carbon dioxide in the oxygen-containing gas vented from the steam catalytic cracking reactor;
   after determining when the regeneration is completed, ceasing the flow of oxygen-containing gas to the steam catalytic cracking reactor; and
   and restarting flow of the hydrocarbon feed.

19. The process of claim 18, wherein determining when the regeneration is completed comprises determining when the concentration of the carbon dioxide in the oxygen-containing gas vented from the steam catalytic cracking reactor is in a range of from 0.05 wt. % to 0.2 wt. % based on the unit weight of the oxygen-containing gas vented from the steam catalytic cracking reactor.

20. A process for upgrading a hydrocarbon feed, the process comprising:
   configuring a steam catalytic cracking reactor in either an ethylene-selective mode or a propylene-selective mode, where configuring the steam catalytic cracking reactor comprises:
      selecting a configuration for the steam catalytic cracking reactor;
      selecting one or more settings for the steam catalytic cracking reactor;
      loading a cracking catalyst based on the one or more steam catalytic cracking reactor settings;
      loading an inert carrier pre-heating into the steam catalytic cracking reactor;
      adjusting a temperature for the steam catalytic cracking reactor based on the one or more steam catalytic cracking reactor settings; and
      adjusting a liquid hourly volumetric space velocity for one or more feed pumps in the steam catalytic cracking reactor; and
   contacting the hydrocarbon feed with steam in the presence of the cracking catalyst in the steam catalytic cracking reactor at reaction conditions sufficient to cause at least a portion of the hydrocarbons in the hydrocarbon feed to undergo one or more cracking reactions to produce a steam catalytic cracking effluent comprising ethylene, propylene, or both.

* * * * *